United States Patent
Binette et al.

(10) Patent No.: US 10,583,220 B2
(45) Date of Patent: Mar. 10, 2020

(54) METHOD AND APPARATUS FOR RESURFACING AN ARTICULAR SURFACE

(75) Inventors: Francois Binette, Weymouth, MA (US); Ed Yiling Lu, Chestnut Hill, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 742 days.

(21) Appl. No.: 10/638,562

(22) Filed: Aug. 11, 2003

(65) Prior Publication Data

US 2005/0038520 A1    Feb. 17, 2005

(51) Int. Cl.
*A61F 2/30*         (2006.01)
*A61L 27/36*        (2006.01)
*A61L 27/38*        (2006.01)
*A61B 17/00*        (2006.01)
(Continued)

(52) U.S. Cl.
CPC ...... *A61L 27/3654* (2013.01); *A61F 2/30756* (2013.01); *A61L 27/38* (2013.01); *A61B 17/00491* (2013.01); *A61B 17/0642* (2013.01); *A61B 2017/00004* (2013.01); *A61F 2/3859* (2013.01); *A61F 2002/30062* (2013.01); *A61F 2002/30225* (2013.01); *A61F 2002/30677* (2013.01); *A61F 2002/30751* (2013.01); *A61F 2002/30764* (2013.01); *A61F 2002/30766* (2013.01); *A61F 2210/0004* (2013.01); *A61F 2230/0069* (2013.01)

(58) Field of Classification Search
CPC .......... A61F 2/4618; A61F 2310/00964; A61F 2002/30764; A61F 2002/30766; A61F 2002/30762; A61F 2002/30761

USPC ................................. 623/14.12, 23.72–23.76
See application file for complete search history.

(56) References Cited

U.S. PATENT DOCUMENTS

| | | | |
|---|---|---|---|
| 206,200 A | 7/1878 | Stewart | |
| 224,226 A | 2/1880 | Rind | |
| 259,260 A | 6/1882 | Baeyer et al. | |

(Continued)

FOREIGN PATENT DOCUMENTS

| | | |
|---|---|---|
| AU | 717552 B2 | 3/2000 |
| CA | 2247158 A1 | 8/1997 |

(Continued)

OTHER PUBLICATIONS

Albrecht et al. "Closure of Osteochondral Lesions Using Chondral Fragments and fibrin Adhesive", Archives of Orthopaedic and Traumatic Surgery, 1983 101: 213-217.*

(Continued)

*Primary Examiner* — Brian E Pellegrino

(57) ABSTRACT

A biocompatible, bioresorbable tissue repair implant or scaffold device is provided for use in repairing a variety of cartilage tissue injuries, and particularly for resurfacing and/or repairing damaged or diseased cartilage. The repair procedures may be conducted with tissue repair implants that contain a biological component that assists in delaying or arresting the progression of degenerative joint diseases and in enhancing tissue healing or repair. The biocompatible, bioresorbable tissue repair implants include a scaffold and particles of viable tissue derived from cartilage tissue, such that the tissue and the scaffold become associated. The particles of living tissue contain one or more viable cells that can migrate from the tissue and populate the scaffold.

7 Claims, 1 Drawing Sheet

(51) Int. Cl.
  *A61B 17/064* (2006.01)
  *A61F 2/38* (2006.01)

(56) References Cited

U.S. PATENT DOCUMENTS

| | | |
|---|---|---|
| 3,272,204 A | 9/1966 | Artandi |
| 3,562,820 A | 2/1971 | Bernhard |
| 3,739,402 A | 6/1973 | Cooley et al. |
| 3,812,017 A | 5/1974 | Santangelo et al. |
| 3,857,932 A | 12/1974 | Shepherd et al. |
| 4,045,418 A | 8/1977 | Sinclair |
| 4,057,537 A | 11/1977 | Sinclair |
| 4,105,034 A | 8/1978 | Shalaby et al. |
| 4,130,639 A | 12/1978 | Shalaby et al. |
| 4,130,689 A | 12/1978 | Costa, Jr. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,344,193 A | 8/1982 | Kenny |
| 4,520,821 A | 6/1985 | Schmidt et al. |
| 4,553,272 A | 11/1985 | Mears |
| 4,585,458 A | 4/1986 | Kurland |
| 4,597,766 A | 7/1986 | Hilal et al. |
| 4,609,551 A | 9/1986 | Caplan et al. |
| 4,728,329 A | 3/1988 | Mansat et al. |
| 4,801,299 A | 1/1989 | Brendel et al. |
| 4,837,285 A | 6/1989 | Berg et al. |
| 4,902,508 A | 2/1990 | Badylak et al. |
| 4,917,700 A | 4/1990 | Aikins |
| 4,946,377 A | 8/1990 | Kovach |
| 5,007,934 A | 4/1991 | Stone |
| 5,041,138 A | 8/1991 | Vacanti et al. |
| 5,053,050 A | 10/1991 | Itay |
| 5,061,281 A | 10/1991 | Mares et al. |
| 5,078,744 A | 1/1992 | Chvapil |
| 5,108,807 A | 4/1992 | Tucker |
| 5,108,989 A | 4/1992 | Amento et al. |
| 5,147,400 A | 9/1992 | Kaplan et al. |
| 5,176,708 A | 1/1993 | Frey et al. |
| 5,206,023 A | 4/1993 | Hunziker et al. |
| 5,258,028 A | 11/1993 | Ersek et al. |
| 5,263,984 A | 11/1993 | Li et al. |
| 5,290,494 A | 3/1994 | Coombes et al. |
| 5,306,311 A | 4/1994 | Stone et al. |
| 5,320,624 A | 6/1994 | Kaplan et al. |
| 5,320,646 A | 6/1994 | Patton et al. |
| 5,326,357 A | 7/1994 | Kandel et al. |
| 5,366,756 A | 11/1994 | Chesterfield et al. |
| 5,393,594 A | 2/1995 | Koyfman et al. |
| 5,425,766 A | 6/1995 | Bowald et al. |
| 5,443,950 A | 8/1995 | Naughton et al. |
| 5,445,833 A | 8/1995 | Badylak et al. |
| 5,455,041 A | 10/1995 | Genco et al. |
| 5,464,929 A | 11/1995 | Bezwada et al. |
| 5,468,253 A | 11/1995 | Bezwada et al. |
| 5,480,827 A | 1/1996 | Guillemin et al. |
| 5,487,897 A | 1/1996 | Polson et al. |
| 5,514,181 A | 5/1996 | Light et al. |
| 5,514,378 A | 5/1996 | Mikos et al. |
| 5,571,189 A | 11/1996 | Kuslich |
| 5,577,517 A | 11/1996 | Bonutti |
| 5,589,176 A | 12/1996 | Seare, Jr. |
| 5,595,751 A | 1/1997 | Bezwada et al. |
| 5,597,579 A | 1/1997 | Bezwada et al. |
| 5,607,687 A | 3/1997 | Bezwada et al. |
| 5,612,028 A | 3/1997 | Sackier et al. |
| 5,618,552 A | 4/1997 | Bezwada et al. |
| 5,620,698 A | 4/1997 | Bezwada et al. |
| 5,624,463 A | 4/1997 | Stone et al. |
| 5,626,611 A | 5/1997 | Liu et al. |
| 5,632,745 A | 5/1997 | Schwartz |
| 5,645,850 A | 7/1997 | Bezwada et al. |
| 5,648,088 A | 7/1997 | Bezwada et al. |
| 5,654,135 A | 8/1997 | Tinois et al. |
| 5,656,492 A | 8/1997 | Glowacki et al. |
| 5,677,355 A | 10/1997 | Shalaby et al. |
| 5,681,353 A | 10/1997 | Li et al. |
| 5,697,976 A | 12/1997 | Chesterfield et al. |
| 5,698,213 A | 12/1997 | Jamiolkowski et al. |
| 5,700,583 A | 12/1997 | Jamiolkowski et al. |
| 5,705,181 A | 1/1998 | Cooper et al. |
| 5,709,854 A | 1/1998 | Griffith-Cima et al. |
| 5,711,960 A | 1/1998 | Shikinami |
| 5,713,920 A | 2/1998 | Bezwada et al. |
| 5,720,969 A | 2/1998 | Gentile et al. |
| 5,723,331 A | 3/1998 | Tubo et al. |
| 5,735,903 A | 4/1998 | Li et al. |
| 5,736,372 A | 4/1998 | Vacanti et al. |
| 5,755,791 A | 5/1998 | Whitson et al. |
| 5,759,190 A | 6/1998 | Vibe-Hansen et al. |
| 5,766,631 A | 6/1998 | Arnold et al. |
| 5,769,899 A | 6/1998 | Schwartz et al. |
| 5,782,914 A | 7/1998 | Schankereli |
| 5,786,217 A | 7/1998 | Tubo et al. |
| 5,800,537 A * | 9/1998 | Bell .......................... 424/93.1 |
| 5,800,543 A | 9/1998 | McLeod et al. |
| 5,830,493 A | 11/1998 | Yokota et al. |
| 5,837,235 A | 11/1998 | Mueller et al. |
| 5,837,278 A | 11/1998 | Geistlich et al. |
| 5,842,477 A | 12/1998 | Naughton et al. |
| 5,855,608 A | 1/1999 | Brekke et al. |
| 5,859,150 A | 1/1999 | Jamiolkowski et al. |
| 5,891,558 A | 4/1999 | Bell et al. |
| 5,902,741 A | 5/1999 | Purchio et al. |
| 5,904,716 A | 5/1999 | Gendler |
| 5,904,717 A | 5/1999 | Brekke et al. |
| 5,914,121 A | 6/1999 | Robey et al. |
| 5,922,025 A | 7/1999 | Hubbard |
| 5,964,805 A | 10/1999 | Stone |
| 5,968,096 A | 10/1999 | Whitson et al. |
| 5,980,889 A | 11/1999 | Butler et al. |
| 5,989,269 A | 11/1999 | Vibe-Hansen et al. |
| 5,990,194 A | 11/1999 | Dunn et al. |
| 5,990,378 A | 11/1999 | Ellis et al. |
| 6,001,352 A | 12/1999 | Boyan et al. |
| 6,001,394 A | 12/1999 | Daculsi et al. |
| 6,005,161 A | 12/1999 | Brekke et al. |
| 6,027,742 A | 2/2000 | Lee et al. |
| 6,042,534 A | 3/2000 | Gellman et al. |
| 6,042,610 A | 3/2000 | Li et al. |
| 6,054,122 A | 4/2000 | MacPhee et al. |
| 6,077,989 A | 6/2000 | Kandel et al. |
| 6,080,579 A | 6/2000 | Hanley, Jr. et al. |
| 6,096,532 A | 8/2000 | Armstrong et al. |
| 6,103,255 A | 8/2000 | Levene et al. |
| 6,110,209 A * | 8/2000 | Stone .................. 623/16.11 |
| 6,110,212 A | 8/2000 | Gregory |
| 6,113,640 A | 9/2000 | Yang et al. |
| 6,117,166 A | 9/2000 | Winston et al. |
| 6,120,514 A | 9/2000 | Vibe-Hansen et al. |
| 6,121,042 A | 9/2000 | Peterson et al. |
| 6,123,727 A | 9/2000 | Vacanti et al. |
| 6,132,463 A | 10/2000 | Lee et al. |
| 6,132,468 A | 10/2000 | Mansmann |
| 6,139,578 A | 10/2000 | Lee et al. |
| 6,140,039 A | 10/2000 | Naughton et al. |
| 6,143,293 A | 11/2000 | Weiss et al. |
| 6,147,135 A | 11/2000 | Yuan et al. |
| 6,153,292 A | 11/2000 | Bell et al. |
| 6,156,068 A | 12/2000 | Walter et al. |
| 6,165,217 A | 12/2000 | Hayes |
| 6,171,338 B1 | 1/2001 | Talja et al. |
| 6,176,880 B1 | 1/2001 | Plouhar et al. |
| 6,179,840 B1 | 1/2001 | Bowman |
| 6,179,872 B1 | 1/2001 | Bell et al. |
| 6,180,007 B1 | 1/2001 | Gentile et al. |
| 6,183,737 B1 | 2/2001 | Zaleske et al. |
| 6,187,053 B1 | 2/2001 | Minuth et al. |
| 6,187,329 B1 | 2/2001 | Agrawal et al. |
| 6,197,061 B1 | 3/2001 | Masuda et al. |
| 6,197,325 B1 | 3/2001 | MacPhee et al. |
| 6,200,606 B1 | 3/2001 | Peterson et al. |
| 6,214,045 B1 | 4/2001 | Corbitt, Jr. et al. |

(56) References Cited

U.S. PATENT DOCUMENTS

| | | | |
|---|---|---|---|
| 6,214,055 B1 | 4/2001 | Simionescu et al. | |
| 6,242,247 B1 * | 6/2001 | Rieser et al. | 435/297.1 |
| 6,251,673 B1 | 6/2001 | Winkler et al. | |
| 6,277,151 B1 | 8/2001 | Lee et al. | |
| 6,283,980 B1 | 9/2001 | Vibe-Hansen et al. | |
| 6,287,316 B1 | 9/2001 | Agarwal et al. | |
| 6,287,340 B1 | 9/2001 | Altman et al. | |
| 6,291,240 B1 | 9/2001 | Mansbridge et al. | |
| 6,306,177 B1 | 10/2001 | Felt et al. | |
| 6,306,424 B1 | 10/2001 | Vyakarnam et al. | |
| 6,316,692 B1 | 11/2001 | Readhead et al. | |
| 6,319,712 B1 | 11/2001 | Meenen et al. | |
| 6,328,765 B1 | 12/2001 | Hardwick et al. | |
| 6,331,312 B1 | 12/2001 | Lee et al. | |
| 6,333,029 B1 | 12/2001 | Vyakarnam et al. | |
| 6,365,149 B2 | 4/2002 | Vyakarnam et al. | |
| 6,378,527 B1 | 4/2002 | Hungerford et al. | |
| 6,378,572 B1 | 4/2002 | Neubauer et al. | |
| 6,379,367 B1 | 4/2002 | Vibe-Hansen et al. | |
| 6,464,729 B1 | 10/2002 | Kandel | |
| 6,485,723 B1 | 11/2002 | Badylak et al. | |
| 6,489,165 B2 | 12/2002 | Bhatnagar et al. | |
| 6,503,278 B1 | 1/2003 | Pohjonen et al. | |
| 6,511,511 B1 | 1/2003 | Slivka et al. | |
| 6,511,958 B1 | 1/2003 | Atkinson et al. | |
| 6,521,430 B1 | 2/2003 | Orwar et al. | |
| 6,530,956 B1 | 3/2003 | Mansmann | |
| 6,534,084 B1 | 3/2003 | Vyakarnam et al. | |
| 6,541,024 B1 | 4/2003 | Kadiyala et al. | |
| 6,551,355 B1 | 4/2003 | Lewandrowski et al. | |
| 6,569,172 B2 | 5/2003 | Asculai et al. | |
| 6,592,588 B1 | 7/2003 | Bobic et al. | |
| 6,599,323 B2 | 7/2003 | Melican et al. | |
| 6,605,294 B2 | 8/2003 | Sawhney | |
| 6,626,950 B2 | 9/2003 | Brown et al. | |
| 6,652,450 B2 | 11/2003 | Neisz et al. | |
| 6,652,585 B2 | 11/2003 | Lange | |
| 6,727,224 B1 | 4/2004 | Zhang et al. | |
| 6,773,458 B1 | 8/2004 | Brauker et al. | |
| 6,783,712 B2 | 8/2004 | Slivka et al. | |
| 6,840,962 B1 | 1/2005 | Vacanti et al. | |
| 6,852,330 B2 | 2/2005 | Bowman et al. | |
| 6,866,681 B2 | 3/2005 | Laboureau et al. | |
| 6,884,428 B2 | 4/2005 | Binette et al. | |
| 6,886,568 B2 | 5/2005 | Frondoza et al. | |
| 6,886,569 B2 | 5/2005 | Chervitz et al. | |
| 6,902,932 B2 | 6/2005 | Altman et al. | |
| 7,109,034 B2 | 9/2006 | Orwar et al. | |
| 7,208,177 B2 * | 4/2007 | Geistlich et al. | 424/484 |
| 7,262,020 B2 | 8/2007 | Hellerstein | |
| 7,316,822 B2 | 1/2008 | Binette et al. | |
| 7,368,124 B2 | 5/2008 | Chun et al. | |
| 7,456,012 B2 | 11/2008 | Ryttsen et al. | |
| 7,799,089 B2 | 9/2010 | Plouhar et al. | |
| 7,824,701 B2 | 11/2010 | Binette et al. | |
| 7,875,296 B2 | 1/2011 | Binette et al. | |
| 7,901,461 B2 | 3/2011 | Harmon et al. | |
| 8,137,686 B2 | 3/2012 | Kladakis et al. | |
| 8,137,702 B2 | 3/2012 | Binette et al. | |
| 8,197,837 B2 | 6/2012 | Jamiolkowski et al. | |
| 8,221,780 B2 | 7/2012 | Dhanaraj et al. | |
| 8,226,715 B2 | 7/2012 | Hwang et al. | |
| 8,496,970 B2 | 7/2013 | Binette et al. | |
| 8,637,066 B2 | 1/2014 | Binnette et al. | |
| 8,641,775 B2 | 2/2014 | Harmon et al. | |
| 2001/0014475 A1 | 8/2001 | Frondoza et al. | |
| 2001/0016353 A1 | 8/2001 | Janas et al. | |
| 2001/0016772 A1 | 8/2001 | Lee et al. | |
| 2001/0023373 A1 | 9/2001 | Plouhar et al. | |
| 2001/0033857 A1 | 10/2001 | Vyakarnam et al. | |
| 2001/0038848 A1 | 11/2001 | Donda et al. | |
| 2001/0039453 A1 | 11/2001 | Gresser et al. | |
| 2001/0051834 A1 | 12/2001 | Frondoza et al. | |
| 2001/0053353 A1 | 12/2001 | Griffith et al. | |
| 2001/0053839 A1 | 12/2001 | Noishiki et al. | |
| 2002/0006428 A1 | 1/2002 | Mahmood et al. | |
| 2002/0009477 A1 | 1/2002 | Mahmood et al. | |
| 2002/0009805 A1 | 1/2002 | Nevo et al. | |
| 2002/0013627 A1 | 1/2002 | Geistlich et al. | |
| 2002/0015719 A1 | 2/2002 | Kellner et al. | |
| 2002/0022883 A1 | 2/2002 | Burg | |
| 2002/0022884 A1 | 2/2002 | Mansmann | |
| 2002/0028192 A1 | 3/2002 | Dimitrijevich et al. | |
| 2002/0029055 A1 | 3/2002 | Bonutti | |
| 2002/0062151 A1 | 5/2002 | Altman et al. | |
| 2002/0082631 A1 | 6/2002 | Bonutti | |
| 2002/0083479 A1 | 6/2002 | Winston et al. | |
| 2002/0091403 A1 | 7/2002 | Bonutti | |
| 2002/0091406 A1 | 7/2002 | Bonutti | |
| 2002/0099401 A1 | 7/2002 | Bonutti | |
| 2002/0099448 A1 | 7/2002 | Hiles et al. | |
| 2002/0107570 A1 | 8/2002 | Sybert et al. | |
| 2002/0119177 A1 | 8/2002 | Bowman et al. | |
| 2002/0120348 A1 | 8/2002 | Melican et al. | |
| 2002/0123750 A1 | 9/2002 | Eisermann et al. | |
| 2002/0127265 A1 | 9/2002 | Bowman et al. | |
| 2002/0133229 A1 | 9/2002 | Laurencin et al. | |
| 2002/0133235 A1 | 9/2002 | Hungerford et al. | |
| 2002/0009806 A1 | 10/2002 | Hicks | |
| 2002/0150604 A1 | 10/2002 | Yi et al. | |
| 2002/0151975 A1 | 10/2002 | Farr, II et al. | |
| 2002/0173558 A1 | 11/2002 | Williams et al. | |
| 2002/0176893 A1 | 11/2002 | Wironen et al. | |
| 2002/0177224 A1 | 11/2002 | Madry et al. | |
| 2003/0004578 A1 | 1/2003 | Brown et al. | |
| 2003/0012805 A1 | 1/2003 | Chen et al. | |
| 2003/0023316 A1 | 1/2003 | Brown et al. | |
| 2003/0003153 A1 | 2/2003 | Asculai et al. | |
| 2003/0026787 A1 | 2/2003 | Fearnot et al. | |
| 2003/0027332 A1 | 2/2003 | Lafrance et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 * | 2/2003 | Schwartz et al. | 623/23.63 |
| 2003/0045937 A1 | 3/2003 | Ginn | |
| 2003/0050709 A1 | 3/2003 | Noth et al. | |
| 2003/0064917 A1 | 4/2003 | Crawford et al. | |
| 2003/0075822 A1 | 4/2003 | Slivka et al. | |
| 2003/0077311 A1 | 4/2003 | Vyakarnam et al. | |
| 2003/0078617 A1 | 4/2003 | Schwartz et al. | |
| 2003/0147935 A1 | 8/2003 | Binette et al. | |
| 2003/0193104 A1 | 10/2003 | Melican et al. | |
| 2004/0024457 A1 | 2/2004 | Boyce et al. | |
| 2004/0059416 A1 * | 3/2004 | Murray et al. | 623/13.15 |
| 2004/0078077 A1 | 4/2004 | Binette et al. | |
| 2004/0078090 A1 | 4/2004 | Binette et al. | |
| 2004/0175408 A1 | 9/2004 | Chun et al. | |
| 2004/0219182 A1 * | 11/2004 | Gomes et al. | 424/423 |
| 2004/0236424 A1 | 11/2004 | Berez et al. | |
| 2004/0249457 A1 | 12/2004 | Smith et al. | |
| 2004/0267088 A1 | 12/2004 | Kammerer | |
| 2004/0267362 A1 | 12/2004 | Hwang et al. | |
| 2005/0002915 A1 | 1/2005 | Atala et al. | |
| 2005/0038520 A1 | 2/2005 | Binette et al. | |
| 2005/0048651 A1 | 3/2005 | Ryttsen et al. | |
| 2005/0113937 A1 | 5/2005 | Binette et al. | |
| 2005/0113938 A1 | 5/2005 | Jamiolkowski et al. | |
| 2005/0125077 A1 | 6/2005 | Harmon et al. | |
| 2005/0147645 A1 | 7/2005 | Budny | |
| 2005/0177249 A1 | 8/2005 | Kladakis et al. | |
| 2005/0232967 A1 | 10/2005 | Kladakis et al. | |
| 2005/0234549 A1 | 10/2005 | Kladakis et al. | |
| 2006/0067967 A1 | 3/2006 | Bowman | |
| 2006/0084930 A1 | 4/2006 | Dhanaraj et al. | |
| 2006/0204439 A1 | 9/2006 | Hellerstein | |
| 2006/0223177 A1 | 10/2006 | Harris et al. | |
| 2006/0280768 A1 | 12/2006 | Hwang et al. | |
| 2006/0293760 A1 | 12/2006 | DeDeyne | |
| 2007/0031470 A1 | 2/2007 | Kladakis et al. | |
| 2007/0036767 A1 | 2/2007 | Mistry et al. | |
| 2007/0250177 A1 | 10/2007 | Bilbo | |
| 2008/0039955 A1 * | 2/2008 | Hunziker | 623/23.76 |
| 2008/0071385 A1 | 3/2008 | Binette et al. | |
| 2008/0226870 A1 | 9/2008 | Sypeck et al. | |

(56) References Cited

U.S. PATENT DOCUMENTS

| | | | |
|---|---|---|---|
| 2008/0241213 A1 | 10/2008 | Chun et al. | |
| 2011/0009963 A1 | 1/2011 | Binette et al. | |
| 2011/0091517 A1 | 4/2011 | Binette et al. | |
| 2011/0097381 A1 | 4/2011 | Binette et al. | |
| 2011/0110958 A1 | 5/2011 | Qiu et al. | |
| 2011/0177134 A1 | 7/2011 | Harmon et al. | |
| 2012/0156265 A1 | 6/2012 | Binette et al. | |
| 2012/0165939 A1 | 6/2012 | Kladakis et al. | |
| 2012/0253464 A1 | 10/2012 | Hwang et al. | |
| 2013/0123937 A1 | 5/2013 | Jamiolkowski et al. | |

FOREIGN PATENT DOCUMENTS

| | | |
|---|---|---|
| DE | 19812195 A1 | 9/1999 |
| EP | 0145492 A2 | 6/1985 |
| EP | 0274898 A2 | 7/1988 |
| EP | 0277678 A1 | 8/1988 |
| EP | 0 411 545 A1 | 2/1991 |
| EP | 0 466 105 A2 | 1/1992 |
| EP | 0464163 A1 | 1/1992 |
| EP | 0 485 215 A1 | 5/1992 |
| EP | 0562864 A1 | 9/1993 |
| EP | 0955024 A2 | 11/1999 |
| EP | 1027897 A1 | 8/2000 |
| EP | 1064958 A1 | 1/2001 |
| EP | 1 074 270 A1 | 2/2001 |
| EP | 1167517 A1 | 1/2002 |
| EP | 1177800 A1 | 2/2002 |
| EP | 1 216 717 A1 | 6/2002 |
| EP | 1216718 A1 | 6/2002 |
| EP | 1348451 A1 | 10/2003 |
| EP | 1 410 811 A1 | 4/2004 |
| EP | 1405649 A1 | 4/2004 |
| EP | 1506790 A1 | 2/2005 |
| EP | 1537839 A1 | 6/2005 |
| EP | 1604622 A1 | 12/2005 |
| FR | 2688690 A1 | 9/1993 |
| GB | 1008193 A | 10/1965 |
| JP | 63-203154 | 8/1988 |
| JP | 63-203154 A | 8/1988 |
| JP | 02-052648 | 2/1990 |
| JP | 2143945 | 12/1990 |
| JP | 19900227442 A | 4/1992 |
| JP | 19900256824 A | 5/1992 |
| JP | H04-502715 A | 5/1992 |
| JP | 19910261753 A | 7/1993 |
| JP | 19920094329 A | 11/1993 |
| JP | 10234844 A | 9/1998 |
| JP | 11-319068 A | 11/1999 |
| JP | 19980129048 A | 11/1999 |
| JP | H11-512626 A | 11/1999 |
| JP | 19980319783 A | 5/2000 |
| JP | 3-139361 B2 | 2/2001 |
| JP | 2001-079079 A | 3/2001 |
| JP | 2001129073 A | 5/2001 |
| JP | 2002-527402 A | 8/2002 |
| JP | 2002-272833 A | 9/2002 |
| JP | 2002-535378 A | 10/2002 |
| JP | 2003320008 A | 11/2003 |
| JP | 2004008437 A | 1/2004 |
| JP | 20020165345 A | 1/2004 |
| JP | 2004-195103 | 7/2004 |
| JP | 2005-237476 A | 9/2005 |
| JP | 4-300557 B2 | 7/2009 |
| RU | 2187261 | 8/2002 |
| SU | 1535542 | 1/1990 |
| WO | 8600533 A1 | 1/1986 |
| WO | 9206179 A1 | 4/1992 |
| WO | 9302718 A1 | 2/1993 |
| WO | 9311805 A1 | 6/1993 |
| WO | 9533821 A1 | 12/1995 |
| WO | 9608277 A1 | 3/1996 |
| WO | 9730662 A1 | 8/1997 |
| WO | 9746665 A1 | 12/1997 |
| WO | 9848860 A1 | 11/1998 |
| WO | 9853768 A1 | 12/1998 |
| WO | 9905992 A1 | 2/1999 |
| WO | 9916381 A1 | 4/1999 |
| WO | 9939724 A1 | 8/1999 |
| WO | 9947097 A2 | 9/1999 |
| WO | 9959647 A1 | 11/1999 |
| WO | 0015248 A2 | 3/2000 |
| WO | 0016381 | 3/2000 |
| WO | WO 00/69355 | 11/2000 |
| WO | 0072782 A1 | 12/2000 |
| WO | 0074741 A2 | 12/2000 |
| WO | 0115753 A1 | 3/2001 |
| WO | WO 01/34065 A1 | 5/2001 |
| WO | 0185226 A1 | 11/2001 |
| WO | 0205750 A2 | 1/2002 |
| WO | 2002000272 A2 | 1/2002 |
| WO | WO 02/30324 | 4/2002 |
| WO | 02062357 A1 | 8/2002 |
| WO | 02074356 A1 | 9/2002 |
| WO | WO 02/096268 A2 | 12/2002 |
| WO | 03/007784 A2 | 1/2003 |
| WO | 03/007786 A2 | 1/2003 |
| WO | 03/007787 A2 | 1/2003 |
| WO | 03/007788 A2 | 1/2003 |
| WO | 03/007790 A2 | 1/2003 |
| WO | 03/007805 A2 | 1/2003 |
| WO | 03/007839 A2 | 1/2003 |
| WO | 03/007847 A1 | 1/2003 |
| WO | 03007789 A2 | 1/2003 |
| WO | 03017826 A2 | 3/2003 |
| WO | 03043674 A1 | 5/2003 |
| WO | 2004012782 A1 | 2/2004 |

OTHER PUBLICATIONS www.btc-bti.com/applications/cryogenicstorage.htm, 6 pgs, printed Jan. 11, 2010.* www.bio-medicine.org/medicine-technology-1/New-Study-Shows-Cloning-From-Dried-Cells-Now-Possible-2988-1/, 2 pgs, printed Jan. 11, 2010.* http://onelook.com/?w=lyophilization&ls=a, printed Jan. 16, 2012.*

Meaney, M. et al. "The migration of cells from the ruptured human anterior cruciate ligament into collagen-glycosaminoglycan regeneration templtes in vitro" *Biomaterials*, 22: 2393-2402 (2001).

Bonisch, M., et al. "Septumredonstrucktion mit PDS-Folie" HNO 47: 1999 pp. 546-550.

Eckersberger, M.D., Franz, "Circumferential tracheal replacement with costal cartilage", The Journal of Thoracic and Cardiovascular Surgery, 1987;94: pp. 175-180.

Matsuo, M.D., Kiyoshi et al., "Semiquantitative Correction of Posttraumatic Enophthalmos with Sliced Cartilage Grafts" Plastic and Reconstructive Surgery, vol. 83, No. 3, Postraumatic Enophthalmos, pp. 429-437.

Megumi, M.D., Yoshikazu, "Augmentation Rhinoplasty with Soft Tissue and Cartilage" Aesthetic Plastic Surgery, 1988, pp. 89-933.

Papadopulos, M.D., Angel, "Compound Implant to Projedt the Nasal Tip" Aesthetic Plastic Surgery, 1987, pp. 181-185.

Partial European Search Report, for EP 04 25 7515, dated May 9, 2005.

Powers, Dennis L. et al., "A cartilagenous graft as an adjunct to finger joint implant arthroplasty" Journal of Biomedical Materials Research, vol. 19, 1985 pp. 509-518.

Rohrbach, Jens Martin et al., "Biological Corneal Replacement— Alternative to Keratoplasty and Keratoprosthesis? A Pilot Study with Heterologous Hyaline Cartilage in the Rabbit Model", Klin Monatsbl Augenheilkd 207, 1995; pp. 191-196.

Trenite, M.D., G.J. Nolst et al., "Reimplantation of autologous septal cartilage in the growing nasal septum", Rhinology, 25, 1987, pp. 225-236.

Sampath, T. et al., "In vitro transformation of mesenchymal cells derived from embryonic muscle into cartilage in response to extracellular matrix components of bone" *Proc. Natl. Acad. Sci USA*, 81:3419-3423 (1984).

European Search Report for EP 10075307 dated Oct. 6, 2010.

(56) References Cited

OTHER PUBLICATIONS

Albrecht, F.H., "The Closure of Joint Cartilage Defects by Means of Cartilage Fragments and Fibrin Adhesive," Fortschr. Med. 101(37):1650-52 (1983).
Allcock in The Encyclopedia of Polymer Science, vol. 13, pp. 31-41, Wiley Intersciences, John Wiley & Sons, 1988.
Australian Search Report for AU application No. 2006200194, dated Feb. 4, 2008.
Boland et. al., J. Macromol. Sci.-Pure Appl. Chem., 2001, A38(12), p. 1231-1243).
Buschmann et al., J. Orthop. Res. 1992; 10:745-752.
Caterson EJ., et al. "Three-Dimensional Cartilage Formation by Bone Marrow-Derived Cells Seeded in Polylactide/Alginate Amalgam," J Biomed Mater Res. 57(3):394-403 (2001) *(Abstract Only).
De Groot, J.H. et al., "Meniscal tissue regeneration in porous 50/50 copoly(l-lactide/epsilon-caprolactone) implants" Biomaterials, vol. 18, No. 8, 1997, pp. 613-622.
De Groot, J.H. et al., "Use of porous polyurethanes for meniscal reconstruction and meniscal prostheses" Biomaterials, vol. 17, No. 2, 1996, pp. 163-173.
Deuel, T. et al., "Growth Factors in Principles of Tissue Engineering," Second Edition, Academic Press pp. 129-141 (2000).
Dialog English language abstract for DE 19812195.
European Search Report, for EP 03 25 6522, dated Feb. 24, 2004.
European Search Report, for EP Application No. 07252617.1, dated Nov. 2, 2007.
Examination file history of EP 01310810, priority date of Dec. 21, 2000.
Frenkel, S, Ph.D. and Paul E. Di Cesare, M.D., "Degradation and Repair of Articular Cartilage," Frontiers in Bioscience, 4th ed., pp. 671-685, pp. 1-32 (Oct. 15, 1999).
Gooch, K. et al., "Mechanical Forces and Growth Factors Utilized in Tissue Engineering" Frontier in Tissue Engineering, Pergamon Chapter II.3, pp. 61-82 (1998).
Grigolo, B., et al. "Transplantation of Chondrocytes Seeded on a Hyaluronan Derivative (hyaff-11) into Cartilage Defects in Rabbits," Biomaterials 22(17):2417-2424 (2001) *(Abstract Only).
Hutmacher DW., "Scaffold Design and Fabrication Technologies for Engineering Tissues-State of the Art and Future Prospectives", J Biomater Sci Polym Ed, 12(1):107-124 (2001) *(Abstract Only).
Hutmacher DW., "Scaffolds in Tissue Engineering Bone and Cartilage", Biomaterials, 21(24):2529-2543 (2000) *(Abstract Only).
Ibarra, C. M.D. et al. "Tissue-Engineered Meniscus—Cells and Matrix", Tissue Engineering in Orthopedic Surgery 31 (3):411-418 (Jul. 2000).
Ikada, Yoshito, Handbook of Fiber Science and Technology, Edited by Menachem Lewin, Jack Preston, vol. III, Part B, Chapter 8, pp. 253, 289-295, Published by M. Dekker, 1983.
International Patent Classification A61L (7th Edition, 1999).
International Patent Classification D04B (7th Edition, 1999).
Journal of Biomaterials Research, vol. 22, pp. 993-1009, 1988 by Cohn and Younes.
Kemnitzer and Kohn, in the Handbook of Biodegradable Polymers, edited by Domb, et. al., Hardwood Academic Press, pp. 251-272 (1997).
Koski, J. M.D. et al., "Meniscal Injury and Repair", Orthopedic Clinics of North American, 31(3):419-435 (Jul. 2000).
Koski, J. M.D. et al., "Tissue-Engineered Ligament—Cells, Matrix, and Growth Factors" Tissue Engineering in Orthopedic Surgery, 31(3):437-452 (Jul. 2000).
Kurashina, K. et al. "Osteogenesis in muscle with composite graft of hydroxyapatite and autogenous calvarial periosteum: a preliminary report" Biomaterials (1995) vol. 16, No. 2, pp. 119-123.
Microcellular Foams via Phase Separation, J. Vac. Sci. Technolol., A.T. Young, vol. 4(3), May/Jun. 1986.
Nioshiki Y., "A new trend in hybrid artificial organs" J. Artificial Organs, 1999, vol. 2: pp. 93-96.
Polymer Preprints (ACS Division of Polymer Chemistry), vol. 30(1), p. 498, 1989 by Cohn.

Radice, M. "Hyaluronan-Based Biopolymers as delivery vehicles for Bone-Marrow-Derived Mesenchymal Progenitors", J Biomed Mater Res. 50(2):101-9 (2000) *(Abstract Only).
Rossi, et al., "Embryonic Purkinje Cells Grafted on the Surface of the Cerebellar Cortex Integrate in the Adult Unlesioned Cerebellum," EP J. Neuroscience 4:589-93 (1992).
Schreiber RE., et al. "A Method for Tissue Engineering of cartilage by Cell Seeding on Bioresorbable Scaffolds," Ann NY Acad Sci. 875:394-404 (1999) *(Abstract Only).
Solov'ev et al., "Functional Activity of Hepatocytes in Liver Fragments In Vitro as a Function if Fragment Size and Duration of Culturing" Bull Exp Biol Med. Jun. 2000;129(6):595-7.
Spaans et al. "Solvent-free fabrication of micro-porous polyurethane amide and polyurethane-urea scaffolds for repair and replacement of the knee joint meniscus" Journal of Biomaterials, vol. 21, No. 23, 2000, pp. 2453-2460.
Stone, K. et al. "Meniscal Regeneration with Copolymeric Collagen Scaffolds," American Journal of Sports Medicine 20 (2):104-111 (1992).
Tienen T. G. et al., "A porous polymer scaffold for meniscal lesion repair—A study in dogs" Biomaterials, vol. 24, No. 14, 2003, pp. 2541-2548.
Tozum et al., J Canadian Dental Assoc. Nov. 2003 69(10):664-664h.
Van Susante JLC, et al. "Linkage of Chondroitin-Sulfate to Type I Collagen Scaffolds Stimulates the Bioactivity of Seeded Chondrocytes in Vitro", Biomaterials 22(17):2359-2369 (2001) *(Abstract Only).
Vandorpe, et al in the Handbook of Biodegradable Polymers, edited by Domb, et al., Hardwood Academic Press, pp. 161-182 (1997).
Defrere et al., "Teflon/polyurethane arthroplasty of the knee: the first 2 years preliminary clinical experience in a new concept of artificial resurfacing of full thickness cartilage legions of the knee," Acta Chir. Belg., 1992, vol. 92, No. 5, pp. 217-227.
European Search Report for EP 08075114.2, dated May 12, 2010.
Chen G., Ushida T. and Tateishi T. "A hybrid network of synthetic polymer mesh and collagen sponge," Chem. Commun., 2000, 1505-1506.
Heller: 'Handbook of Biodegradable Polymers', 1997, Hardwood Academic Press pp. 99-118.
Andreasen, J.O. et al. Evaluation of different types of autotransplanted connective tissues as potential periodontal ligament substitues: An experimental replantation study in monkeys, International Journal of Oral Surgery, Jun. 1981, vol. 10, Issue 3, pp. 189-201 (Abstract only).
Andreasen, J.O. et al. Evaluation of different types of autotransplanted connective tissues as potential periodontal ligamant substitues: An experimental replantation study in monkeys, International Journal of Oral Surgery, Jun. 1981, vol. 10, Issue 3, pp. 189-201 (Full text).
Japanese Office Action, from JP 2004-191861, dated Mar. 1, 2011.
Japanese Office Action dated Dec. 6, 2011 for Application No. 2004-233655 (8 Pages).
Japanese Office Action dated Apr. 24, 2012 for Application No. 2007-171032 (6 Pages).
Japanese Office Action dated Feb. 26, 2013 for Application No. 2007-171032 (4 Pages).
[No author listed] Warm Glass Disclosure "The Basic Fusing and Slumping Process." 1999. Retrieved from the internet Nov. 22, 2005.
European Search Report for Application No. 04251265.7 dated Jul. 9, 2004.
European Search Report for Application No. 05256123, dated Feb. 1, 2006.
Guy Fortier, Development of Biosensors Based on Immobilization of Enzymes in Eastman AQ Polymer Coated with a Layer of Nation, Analytical Letters, vol. 23 No. 9, Sep. 1990. Abstract.
Lobler et al., Biomaterial implants induce the inflammation marker CPR at the site of implantation, Journal of Biomedical Materials Research, 2002, vol. 61, No. 1, pp. 165-167.
U.S. Appl. No. 10/383,369, filed Mar. 7, 2003, Method of Preparation of Bioabsorbable Porous Reinforced Tissue Implants and Implants Thereof.
U.S. Appl. No. 10/955,370, filed Sep. 30, 2004, Method of Preparation of Bioabsorbable Porous Reinforced Tissue Implants and Implants Thereof.

(56) References Cited

OTHER PUBLICATIONS

U.S. Appl. No. 12/059,042, filed Mar. 31, 2008, Method of Preparation of Bioabsorbable Porous Reinforced Tissue Implants and Implants Thereof.
U.S. Appl. No. 13/466,448, filed May 8, 2012, Method of Preparation of Bioabsorbable Porous Reinforced Tissue Implants and Implants Thereof.
Japanese Office Action dated Aug. 28, 2012 for Application No. 2004-233655 (6 Pages).
Takeuchi et al., The present situation and vision of joint transplantation. Journal of Clinical and Experimental Medicine. 1995;164(10):748-9. Translation.

* cited by examiner

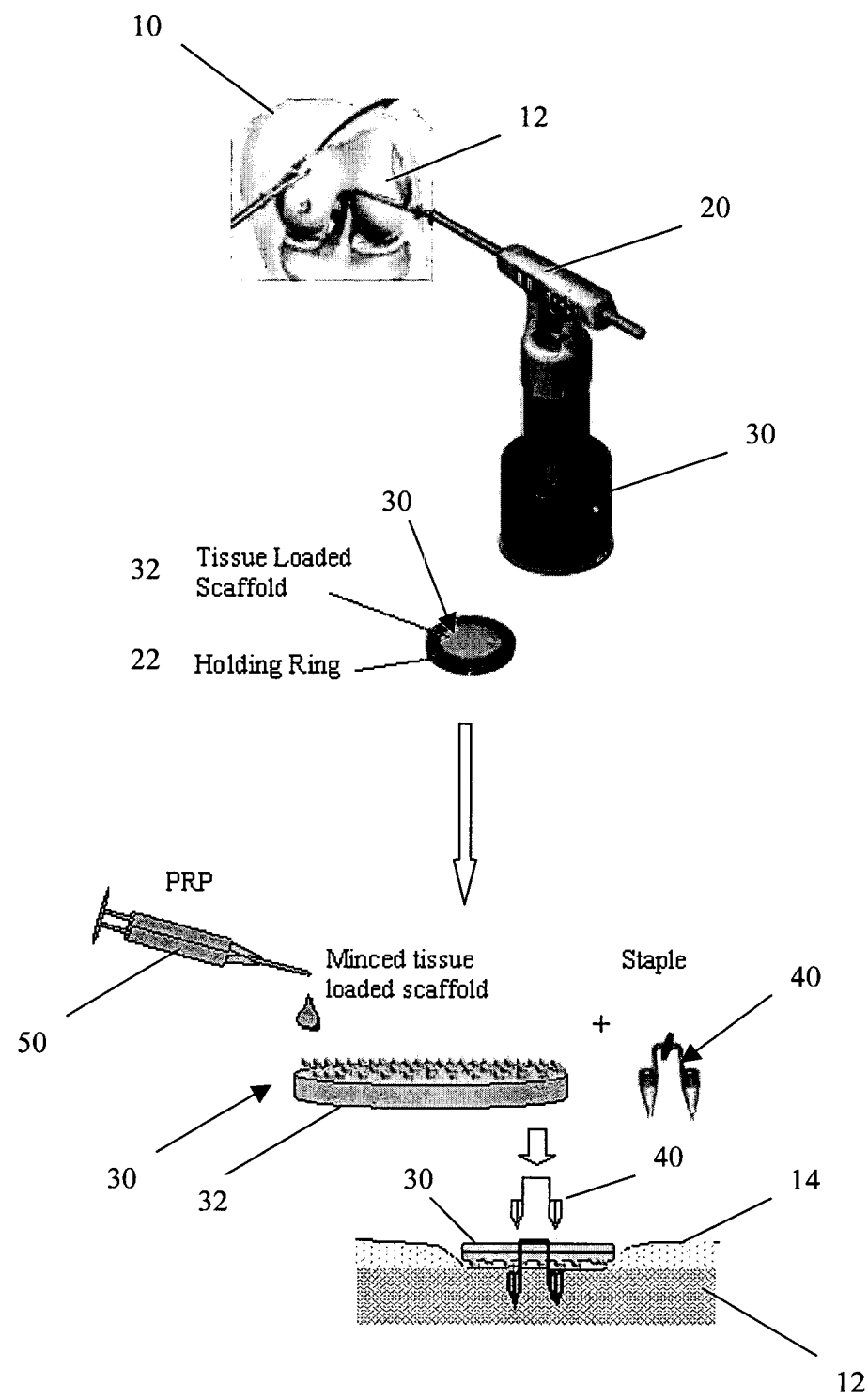

METHOD AND APPARATUS FOR RESURFACING AN ARTICULAR SURFACE

CROSS REFERENCE TO RELATED APPLICATIONS

Not applicable.

STATEMENT REGARDING FEDERALLY SPONSORED RESEARCH

Not applicable.

FIELD OF THE INVENTION

The present invention relates to surgical methods and apparatus, and more particularly to a method for resurfacing and functionally restoring an articular surface of a joint to delay the progression of cartilage damage caused by degenerative joint diseases such as osteoarthritis, and biocompatible, biorebsorbable tissue implant devices useful in such a method.

BACKGROUND OF THE INVENTION

Injuries to soft tissue, such as cartilage, skin, muscle, bone, tendon and ligament, where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques.

One common example of cartilage injury is damage to the menisci of a knee joint. There are two menisci of the knee joint, a medial and a lateral meniscus. Each meniscus is a biconcave, fibrocartilage tissue that is interposed between the femur and tibia of the leg. In addition to the menisci of the knee joint, meniscal cartilage can also be found in the acromioclavicular joint, i.e., the joint between the clavicle and the acromion of the scapula, in the stemoclavicular joint, i.e., the joint between the clavicle and the sternum, and in the temporomandibular joint, i.e., the joint of the lower jaw. The primary functions of meniscal cartilage are to bear loads, to absorb shock and to stabilize a joint. If not treated properly, an injury to the meniscus, such as a "bucket-handle tear" in the knee joint, may lead to the development of osteoarthritis. Current conventional treatment modalities for damaged meniscal cartilage include the removal and/or surgical repair of the damaged cartilage.

One common type of tissue injury at the knee joint involves damage to articular cartilage, a non-vascular, resilient, and flexible connective tissue. Cartilage typically acts as a "shock-absorber" at articulating joints, but some types of cartilage provide support to tubular structures, such as for example, the larynx, air passages, and the ears. In general, cartilage tissue is comprised of cartilage cells, known as chondrocytes, located in an extracellular matrix, which contains collagen, a structural scaffold, and aggrecan, a space-filling proteoglycan. Several types of cartilage can be found in the body, including hyaline cartilage, fibrocartilage and elastic cartilage. Hyaline cartilage can appear in the body as distinct pieces, or alternatively, this type of cartilage can be found fused to the articular ends of bones. Hyaline cartilage is generally found in the body as articular cartilage, costal cartilage, and temporary cartilage (i.e., cartilage that is ultimately converted to bone through the process of ossification). Fibrocartilage is a transitional tissue that is typically located between tendon and bone, bone and bone, and/or hyaline cartilage and hyaline cartilage. Elastic cartilage, which contains elastic fibers distributed throughout the extracellular matrix, is typically found in the epiglottis, the ears and the nose.

One common example of hyaline cartilage injury is a traumatic focal articular cartilage defect to the knee. A strong mechanical or loading impact to the joint can result in the complete or partial detachment or removal of a cartilage fragment of various size and shape. Damaged articular cartilage can severely restrict joint function, cause debilitating pain and may result in long term chronic diseases such as osteoarthritis, which gradually destroys the cartilage and underlying bone of the joint. Injuries to the articular cartilage tissue will not heal spontaneously and require surgical intervention if symptomatic. The current modality of treatment consists of lavage, removal of partially or completely unattached tissue fragments. In addition, the surgeon will often use a variety of methods such as abrasion, drilling or microfractures, to induce bleeding into the cartilage defect and formation of a clot. It is believed that the cells coming from the marrow will form a scar-like tissue called fibrocartilage that can provide temporary relief to some symptoms. Unfortunately, the fibrocartilage tissue does not have the same mechanical properties as hyaline cartilage and degrades faster over time as a consequence of wear. Patients typically have to undergo repeated surgical procedures to relieve reoccurring symptoms, though this type of surgery does not delay or prevent further deterioration of the cartilage surface.

More recently, experimental approaches involving the implantation of autologous chondrocytes have been used with increasing frequency. The process involves the harvest of a small biopsy of articular cartilage in a first surgical procedure, which is then transported to a laboratory specialized in cell culture for amplification. The tissue biopsy is treated with enzymes that will release the chondrocyte cells from the matrix, and the isolated cells will be grown for a period of 3 to 4 weeks using standard tissue culture techniques. Once the cell population has reached a target number, the cells are sent back to the surgeon for implantation during a second surgical procedure. This manual labor-intense process is extremely costly and time consuming. Although, the clinical data suggest long term benefit for the patient, the prohibitive cost of the procedure combined with the traumatic impact of two surgical procedures to the knee, has hampered reasonable acceptance of this technique among patients and doctors.

Other known surgical techniques for the surgical treatment of damaged tissue (e.g., cartilage, meniscal cartilage, ligaments, tendons and skin) include the use of surgical implants. Various surgical implants are known and have been used in surgical procedures to help achieve these benefits. For example, it is known to use various devices and techniques for creating implants having isolated cells loaded onto a delivery vehicle. Such cell-seeded implants are used in an in vitro method of making and/or repairing cartilage by growing cartilaginous structures that consist of chondrocytes seeded onto biodegradable, biocompatible fibrous polymeric matrices. Such methods also require the initial isolation of chondrocytes from cartilaginous tissue prior to the chondrocytes being seeded onto the polymeric matrices. Other techniques for repairing damaged tissue employ implants having stem or progenitor cells that are used to produce the desired tissue. For example, it is known to use stem or progenitor cells, such as the cells within fatty tissue, muscle, or bone marrow, to regenerate bone and/or cartilage in a patient. The stem cells are removed from the patient and placed in an environment favorable to cartilage formation, thereby inducing the fatty tissue cells to proliferate and to create a different type of cell, such as for example, cartilage cells.

While these current treatments address focal point defects, they are not tailored for treating large surface areas of diseased or damaged tissue (e.g., cartilage) that occur with the progression of degenerative joint diseases such as osteoarthritis. Osteoarthritis is a long term degenerative joint disease that results from the breakdown of the joint's cartilage. In patients suffering from osteoarthritis, as the cartilage wears down, the bones rub against each other, damaging the bones and causing pain and limited movement of the joint. Swelling and stiffness of the joint can also occur, along with the creation of bony spurs that can decrease the flexibility in the affected joint. If the disease is advanced or severe enough, the bones of the joint may grow into each other, or fuse together, and result in complete loss of movement.

At the present time, there is no cure for osteoarthritis. Current treatment options focus on slowing down the progression of the disease, pain management and/or improving joint movement. Corticosteroids, glucocorticosteroids, aspirin, ibuprofen, or acetaminophen can be administered, as well as heat/cold therapy for the temporary relief of pain. A typical treatment regimen can include, in addition to the administration of therapeutic agents listed above, physical therapy and regular exercise to keep the joints flexible and improve muscle strength. Weight loss can also reduce excess stress on weight-bearing joints, while splints can be used to protect the joint and prevent further stress or strain. If all attempted treatments fail, surgery may be necessary to fuse, replace or stop deformation in the joints and relieve chronic pain.

Since osteoarthritis is a chronic disease that has a fairly long progression window before a total knee replacement surgery can be recommended, there exists a need for a way to provide early surgical or medical intervention to arrest the progression, and possibly enable the prevention, of the joint's destruction. Furthermore, because current surgical devices and methods of treatment involving osteochondral transplantation and chondrocyte transplantation suffer from setbacks such as incomplete tissue integration and tedious implant manufacturing process and prolonged rehabilitation time, there exists a need for a surgical solution for repairing a cartilage defect spanning a large surface area which overcomes the aforementioned problems.

SUMMARY OF THE INVENTION

This invention relates to a method for resurfacing a large surface area (e.g., greater than about 10 cm$^2$) such as an entire condyle area where both cartilage and subchondral bone tissues have been affected by degeneration such as by osteoarthritis. More specifically, a method is provided for resurfacing an articular surface of a bone joint by replacing damaged or diseased cartilage tissue with a tissue-engineered construct for growing new cartilage tissue. Also provided with this invention are biocompatible, bioresorbable tissue implants for use in treating tissue, and the methods for making and using these implants. For example, the tissue implants can be used for the repair and/or regeneration of diseased or damaged tissue such as damaged cartilage tissue that results from the onset of osteoarthritis. The implants include a biocompatible, bioresorbable scaffold used alone as a regenerative space holder, and can optionally be associated with a suspension containing healthy minced tissue fragments. The biocompatible tissue implants can also include an additional biological agent and/or an optional retaining element placed over the suspension of minced tissue. In an exemplary embodiment where the tissue implant is to repair damaged cartilage tissue of an articular surface, the minced tissue fragment can comprise cartilage tissue containing chondrocytes, or fragments of bone marrow.

The invention also relates to a method of preparing such biocompatible, bioresorbable tissue implants useful as regenerative space holders for cell ingrowth, infiltration or migration. The implants are made by providing at least one biocompatible, bioresorbable scaffold and a sample of minced tissue, processing the tissue sample to create a suspension of viable tissue having at least one kind of tissue fragment, and depositing the tissue sample upon the scaffold. In one embodiment, the method of producing these implants can include the further step of incubating the tissue-laden scaffold in a suitable environment for a duration and under conditions that are sufficient to effectively allow cells within the tissue sample to populate the scaffold.

The invention also relates to methods of treating tissue using the biocompatible, bioresorbable tissue implants of the present invention. Tissue treatment according to these methods can be performed by providing a biocompatible, bioresorbable scaffold and a sample of minced tissue, depositing the tissue sample upon the biocompatible scaffold, and placing the tissue-laden scaffold in a desired position relative to the tissue to be treated. In one embodiment, tissue repair can be achieved by providing a biocompatible scaffold and a sample of minced tissue, depositing the tissue sample in a desired position relative to the tissue injury, and placing the biocompatible scaffold over the tissue. In another embodiment, the method of producing these implants can include the further step of incubating the tissue-laden scaffold in a suitable environment for a duration and under conditions that are effective to allow cells within the tissue sample to populate the scaffold. In yet another embodiment, the methods of treating tissue can also include the additional step of affixing the scaffold in a desired position relative to the tissue to be treated, such as, for example, by fastening the tissue-laden scaffold in place.

In an exemplary embodiment, the implant can be used to resurface large chondral defects. In particular, the implant can be used to treat cartilage defects in a high weight-bearing condyle area in a knee joint resulting from the onset of osteoarthritis.

BRIEF DESCRIPTION OF THE DRAWINGS

The invention can be more fully understood from the following detailed description taken in conjunction with the accompanying exemplary drawing, in which:

FIG. 1 shows a diagram of the method of preparing and attaching a tissue repair implant of the present invention.

DETAILED DESCRIPTION OF THE INVENTION

The present invention provides a tissue-engineered approach to replacing arthritic cartilage resulting from the progression of a degenerative joint disease such as osteoarthritis. The approach involves replacing a large surface area of diseased or damaged cartilage with an implant that is fashioned to provide optimal new cell and tissue growth at the implanted area. The implant comprises a flexible scaffold that can conform to the contours or curvature of the surface area on which the implant is to be fixed, yet provides sufficient mechanical support for cell ingrowth, infiltration or migration. In one embodiment, the present invention provides a surgical approach for preparing, delivering, and fixing a construct that includes the implant of the present invention either impregnated with cartilage tissue, or without any tissue associated with the implant, to a subchondral bone surface where damaged or diseased cartilage has been removed.

In an exemplary method of the present invention, a patient having an isolated cartilage lesion at the articular surface of a bone joint such as the knee is prepared for tissue repair surgery. Through an arthrotomy incision, the knee joint can be opened and the lesion exposed. The arthritic cartilage tissue is removed, along with any fibrillation and fissures on the articular surface. Debridement of the articular surface should be deep enough to expose a subchondral bone surface for receiving the tissue repair implant of the present invention. If desired, holes can be formed on the subchondral bone surface to induce bleeding and effect marrow cell infiltration prior to placement of the implant onto the surface. Once the articular surface has been properly prepared, the tissue repair implant can be implanted onto the prepared articular surface, and secured in place.

The biocompatible, bioresorbable tissue repair implants used for the articular resurfacing of the present invention include a biocompatible, bioresorbable scaffold and, optionally, a suspension of minced tissue having at least one minced tissue fragment, wherein the minced tissue suspension is associated with the scaffold. The minced tissue in the suspension of the present invention includes at least one viable cell that can migrate from the tissue fragment and onto the scaffold.

The scaffold has at least a portion that is in contact with the minced tissue suspension. The minced tissue suspension can be disposed on the outer surface of the scaffold, on an inner region of the scaffold, and any combination thereof, or alternatively, the entire scaffold can be in contact with the minced tissue suspension. The scaffold can be formed using virtually any material or delivery vehicle that is biocompatible, bioimplantable, easily sterilized and that has sufficient structural integrity and physical and/or mechanical properties to effectively provide for ease of handling in an operating room environment and to permit it to accept and retain sutures or other fasteners without substantially tearing. Alternatively, the scaffold could be in the form of an injectable gel that would set in place at the defect site. Sufficient strength and physical properties are developed in the scaffold through the selection of materials used to form the scaffold, and the manufacturing process. Preferably, the scaffold is also pliable so as to allow the scaffold to adjust to the dimensions of the target site of implantation. In some embodiments, the scaffold can be a bioresorbable or bioabsorbable material.

In one embodiment of the present invention, the scaffold can be formed from a biocompatible polymer. A variety of biocompatible polymers can be used to make the biocompatible tissue implants or scaffold devices according to the present invention. The biocompatible polymers can be synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the scaffold includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and blends thereof. Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-,L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α, α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ∈-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997). Polyanhydrides include those derived from diacids of the form $HOOC-C_6H_4-O-(CH_2)_m-O-C_6H_4-COOH$, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al., Hardwood Academic Press, pp. 99-118 (1997).

As used herein, the term "glycolide" is understood to include polyglycolic acid. Further, the term "lactide" is understood to include L-lactide, D-lactide, blends thereof, and lactic acid polymers and copolymers.

Elastomeric copolymers are also particularly useful in the present invention. Suitable elastomeric polymers include those with an inherent viscosity in the range of about 1.2 dL/g to 4 dL/g, more preferably about 1.2 dL/g to 2 dL/g and most preferably about 1.4 dL/g to 2 dL/g as determined at 25° C. in a 0.1 gram per deciliter (g/dL) solution of polymer in hexafluoroisopropanol (HFIP). Further, suitable elastomers exhibit a high percent elongation and a low modulus, while possessing good tensile strength and good recovery characteristics. In the preferred embodiments of this invention, the elastomer exhibits a percent elongation greater than about 200 percent and preferably greater than about 500 percent. In addition to these elongation and modulus properties, suitable elastomers should also have a tensile strength greater than about 500 psi, preferably greater than about 1,000 psi, and a tear strength of greater than about 50 lbs/inch, preferably greater than about 80 lbs/inch.

Exemplary biocompatible elastomers that can be used in the present invention include, but are not limited to, elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable biocompatible elastomers are described in U.S. Pat. No. 5,468,253.

In one embodiment, the elastomer is a copolymer of 35:65 ε-caprolactone and glycolide, formed in a dioxane solvent and including a polydioxanone mesh. In another embodiment, the elastomer is a copolymer of 40:60 ε-caprolactone and lactide with a polydioxanone mesh. In yet another embodiment, the elastomer is a 50:50 blend of a 35:65 copolymer of ε-caprolactone and glycolide and 40:60 copolymer of ε-caprolactone and lactide. The polydioxanone mesh may be in the form of a one layer thick two-dimensional mesh or a multi-layer thick three-dimensional mesh.

The scaffold of the present invention can, optionally, be formed from a bioresorbable or bioabsorbable material that has the ability to resorb in a timely fashion in the body environment. The differences in the absorption time under in vivo conditions can also be the basis for combining two different copolymers when forming the scaffolds of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible scaffold. Depending upon the processing technique used, the two constituents can be either randomly inter-connected bicontinuous phases, or the constituents could have a gradient-like architecture in the form of a laminate type composite with a well integrated interface between the two constituent layers. The microstructure of these scaffolds can be optimized to regenerate or repair the desired anatomical features of the tissue that is being regrown.

In one embodiment, it is desirable to use polymer blends to form scaffolds which transition from one composition to another composition in a gradient-like architecture. Scaffolds having this gradient-like architecture are particularly advantageous in tissue engineering applications to repair or regenerate the structure of naturally occurring tissue such as cartilage (articular, meniscal, septal, tracheal, auricular, costal, etc.), tendon, ligament, nerve, esophagus, skin, bone, and vascular tissue. For example, by blending an elastomer of ε-caprolactone-co-glycolide with ε-caprolactone-co-lactide (e.g., with a mole ratio of about 5:95) a scaffold may be formed that transitions from a softer spongy material to a stiffer more rigid material, for example, in a manner similar to the transition from cartilage to bone. Clearly, one of ordinary skill in the art will appreciate that other polymer blends may be used for similar gradient effects, or to provide different gradients (e.g., different absorption profiles, stress response profiles, or different degrees of elasticity). For example, such design features can establish a concentration gradient for the suspension of minced tissue associated with the scaffolds of the present invention, such that a higher concentration of the tissue fragments is present in one region of the implant (e.g., an interior portion) than in another region (e.g., outer portions).

The biocompatible scaffold of the tissue repair implant of the present invention can also include a reinforcing material comprised of any absorbable or non-absorbable textile having, for example, woven, knitted, warped knitted (i.e., lace-like), non-woven, and braided structures. In one embodiment, the reinforcing material has a mesh-like structure. In any of the above structures, mechanical properties of the material can be altered by changing the density or texture of the material, the type of knit or weave of the material, the thickness of the material, or by embedding particles in the material. The mechanical properties of the material may also be altered by creating sites within the mesh where the fibers are physically bonded with each other or physically bonded with another agent, such as, for example, an adhesive or a polymer. The fibers used to make the reinforcing component can be monofilaments, yarns, threads, braids, or bundles of fibers. These fibers can be made of any biocompatible material including bioabsorbable materials such as polylactic acid (PLA), polyglycolic acid (PGA), polycaprolactone (PCL), polydioxanone (PDO), trimethylene carbonate (TMC), copolymers or blends thereof. These fibers can also be made from any biocompatible materials based on natural polymers including silk and collagen-based materials. These fibers can also be made of any biocompatible fiber that is nonresorbable, such as, for example, polyethylene, polyethylene terephthalate, poly(tetrafluoroethylene), polycarbonate, polypropylene and poly(vinyl alcohol). In one embodiment, the fibers are formed from 95:5 copolymer of lactide and glycolide.

In another embodiment, the fibers that form the reinforcing material can be made of a bioabsorbable glass. Bioglass, a silicate containing calcium phosphate glass, or calcium phosphate glass with varying amounts of solid particles added to control resorption time are examples of materials that could be spun into glass fibers and used for the reinforcing material. Suitable solid particles that may be added include iron, magnesium, sodium, potassium, and combinations thereof.

The biocompatible scaffolds as well as the reinforcing material may also be formed from a thin, perforation-containing elastomeric sheet with pores or perforations to allow tissue ingrowth. Such a sheet could be made of blends or copolymers of polylactic acid (PLA), polyglycolic acid (PGA), polycaprolactone (PCL), and polydioxanone (PDO).

In one embodiment, filaments that form the biocompatible scaffolds or the reinforcing material may be co-extruded to produce a filament with a sheath/core construction. Such filaments are comprised of a sheath of biodegradable polymer that surrounds one or more cores comprised of another biodegradable polymer. Filaments with a fast-absorbing sheath surrounding a slower-absorbing core may be desirable in instances where extended support is necessary for tissue ingrowth.

One of ordinary skill in the art will appreciate that one or more layers of the reinforcing material may be used to reinforce the tissue implant of the invention. In addition, biodegradable textile scaffolds, such as, for example, meshes, of the same structure and chemistry or different structures and chemistries can be overlaid on top of one another to fabricate biocompatible tissue implants with superior mechanical strength.

In embodiments where the scaffold includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof. By way of nonlimiting example, the biocompatible scaffold can be constructed from a collagen-based small intestine submucosa.

In another embodiment of the present invention, the biocompatible scaffold can be formed from a biocompatible ceramic material. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

In yet another embodiment of the tissue implants of the present invention, the scaffold can be formed using tissue grafts, such as may be obtained from autogeneic tissue, allogeneic tissue and xenogeneic tissue. By way of nonlimiting example, tissues such as skin, cartilage, ligament, tendon, periosteum, perichondrium, synovium, fascia, mesenter and sinew can be used as tissue grafts to form the biocompatible scaffold. In some embodiments where an allogeneic tissue is used, tissue from a fetus or newborns can be used to avoid the immunogenicity associated with some adult tissues.

In another embodiment, the scaffold could be in the form of an injectable gel that would set in place at the defect site. The gel can be a biological or synthetic hydrogel, including alginate, cross-linked alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet rich plasma (PRP) clot, platelet poor plasma (PPP) clot, Matrigel, or blends thereof.

In still yet another embodiment of the tissue implants, the scaffold can be formed from a polymeric foam component having pores with an open cell pore structure. The pore size can vary, but preferably, the pores are sized to allow tissue ingrowth. More preferably, the pore size is in the range of about 50 to 1000 microns, and even more preferably, in the range of about 50 to 500 microns. The polymeric foam component can, optionally, contain a reinforcing component, such as for example, the textiles disclosed above. In some embodiments where the polymeric foam component contains a reinforcing component, the foam component can be integrated with the reinforcing component such that the pores of the foam component penetrate the mesh of the reinforcing component and interlock with the reinforcing component.

The foam component of the tissue implant may be formed as a foam by a variety of techniques well known to those having ordinary skill in the art. For example, the polymeric starting materials may be foamed by lyophilization, supercritical solvent foaming (i.e., as described in EP 464,163), gas injection extrusion, gas injection molding or casting with an extractable material (e.g., salts, sugar or similar suitable materials).

In one embodiment, the foam component of the engineered tissue repair implant devices of the present invention may be made by a polymer-solvent phase separation technique, such as lyophilization. Generally, however, a polymer solution can be separated into two phases by any one of the four techniques: (a) thermally induced gelation/crystallization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure with a density less than the bulk polymer and pores in the micrometer ranges. See Microcellular Foams Via Phase Separation, J. Vac. Sci. Technol., A. T. Young, Vol. 4(3), May/June 1986.

The steps involved in the preparation of these foams include choosing the right solvents for the polymers to be lyophilized and preparing a homogeneous solution. Next, the polymer solution is subjected to a freezing and vacuum drying cycle. The freezing step phase separates the polymer solution and vacuum drying step removes the solvent by sublimation and/or drying, leaving a porous polymer structure or an interconnected open cell porous foam.

Suitable solvents that may be used in the preparation of the foam component include, but are not limited to, formic acid, ethyl formate, acetic acid, hexafluoroisopropanol (HFIP), cyclic ethers (e.g., tetrahydrofuran (THF), dimethylene fluoride (DMF), and polydioxanone (PDO)), acetone, acetates of C2 to C5 alcohols (e.g., ethyl acetate and t-butylacetate), glyme (e.g., monoglyme, ethyl glyme, diglyme, ethyl diglyme, triglyme, butyl diglyme and tetraglyme), methylethyl ketone, dipropyleneglycol methyl ether, lactones (e.g., γ-valerolactone, δ-valerolactone, β-butyrolactone, γ-butyrolactone), 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, a preferred solvent is 1,4-dioxane. A homogeneous solution of the polymer in the solvent is prepared using standard techniques.

The applicable polymer concentration or amount of solvent that may be utilized will vary with each system. Generally, the amount of polymer in the solution can vary from about 0.5% to about 90% and, preferably, will vary from about 0.5% to about 30% by weight, depending on factors such as the solubility of the polymer in a given solvent and the final properties desired in the foam.

In one embodiment, solids may be added to the polymer-solvent system to modify the composition of the resulting foam surfaces. As the added particles settle out of solution to the bottom surface, regions will be created that will have the composition of the added solids, not the foamed polymeric material. Alternatively, the added solids may be more concentrated in desired regions (i.e., near the top, sides, or bottom) of the resulting tissue implant, thus causing compositional changes in all such regions. For example, concentration of solids in selected locations can be accomplished by adding metallic solids to a solution placed in a mold made of a magnetic material (or vice versa).

A variety of types of solids can be added to the polymer-solvent system. Preferably, the solids are of a type that will not react with the polymer or the solvent. Generally, the added solids have an average diameter of less than about 1.0 mm and preferably will have an average diameter of about 50 to about 500 microns. Preferably, the solids are present in an amount such that they will constitute from about 1 to about 50 volume percent of the total volume of the particle and polymer-solvent mixture (wherein the total volume percent equals 100 volume percent).

Exemplary solids include, but are not limited to, particles of demineralized bone, calcium phosphate particles, bioglass particles, calcium sulfate, or calcium carbonate particles for bone repair, leachable solids for pore creation and particles of bioabsorbable polymers not soluble in the solvent system that are effective as reinforcing materials or to create pores as they are absorbed, and non-bioabsorbable materials.

Suitable leachable solids include nontoxic leachable materials such as salts (e.g., sodium chloride, potassium chloride, calcium chloride, sodium tartrate, sodium citrate, and the like), biocompatible mono and disaccharides (e.g., glucose, fructose, dextrose, maltose, lactose and sucrose), polysaccharides (e.g., starch, alginate, chitosan), water soluble proteins (e.g., gelatin and agarose). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. Such a process is described in U.S. Pat. No. 5,514,378. Preferably the foam will be dried after the leaching process is complete at low temperature and/or vacuum to minimize hydrolysis of the foam unless accelerated absorption of the foam is desired.

Suitable non-bioabsorbable materials include biocompatible metals such as stainless steel, cobalt chrome, titanium and titanium alloys, and bioinert ceramic particles (e.g., alumina, zirconia, and calcium sulfate particles). Further, the non-bioabsorbable materials may include polymers such as polyethylene, polyvinylacetate, polymethylmethacrylate, polypropylene, poly(ethylene terephthalate), silicone, polyethylene oxide, polyethylene glycol, polyurethanes, polyvinyl alcohol, natural polymers (e.g., cellulose particles, chitin, and keratin), and fluorinated polymers and copolymers (e.g., polyvinylidene fluoride, polytetrafluoroethylene, and hexafluoropropylene).

It is also possible to add solids (e.g., barium sulfate) that will render the tissue implants radio opaque. The solids that may be added also include those that will promote tissue regeneration or regrowth, as well as those that act as buffers, reinforcing materials or porosity modifiers.

As noted above, porous, reinforced tissue repair implant devices of the present invention are made by injecting, pouring, or otherwise placing, the appropriate polymer solution into a mold set-up comprised of a mold and the reinforcing elements of the present invention. The mold set-up is cooled in an appropriate bath or on a refrigerated shelf and then lyophilized, thereby providing a reinforced scaffold. A biological component can be added either before or after the lyophilization step. In the course of forming the foam component, it is believed to be important to control the rate of freezing of the polymer-solvent system. The type of pore morphology that is developed during the freezing step is a function of factors such as the solution thermodynamics, freezing rate, temperature to which it is cooled, concentration of the solution, and whether homogeneous or heterogenous nucleation occurs. One of ordinary skill in the art can readily optimize the parameters without undue experimentation.

The required general processing steps include the selection of the appropriate materials from which the polymeric foam and the reinforcing components are made. If a mesh reinforcing material is used, the proper mesh density must be selected. Further, the reinforcing material must be properly aligned in the mold, the polymer solution must be added at an appropriate rate and, preferably, into a mold that is tilted at an appropriate angle to avoid the formation of air bubbles, and the polymer solution must be lyophilized.

In embodiments that utilize a mesh reinforcing material, the reinforcing mesh has to be of a certain density. That is, the openings in the mesh material must be sufficiently small to render the construct sutureable or otherwise fastenable, but not so small as to impede proper bonding between the foam and the reinforcing mesh as the foam material and the open cells and cell walls thereof penetrate the mesh openings. Without proper bonding the integrity of the layered structure is compromised leaving the construct fragile and difficult to handle. Because the density of the mesh determines the mechanical strength of the construct, the density of the mesh can vary according to the desired use for tissue repair. In addition, the type of weave used in the mesh can determine the directionality of the mechanical strength of the construct, as well as the mechanical properties of the reinforcing material, such as for example, the elasticity, stiffness, burst strength, suture retention strength and ultimate tensile strength of the construct. By way of non-limiting example, the mesh reinforcing material in a foam-based biocompatible scaffold of the present invention can be designed to be stiff in one direction, yet elastic in another, or alternatively, the mesh reinforcing material can be made isotropic.

During the lyophilization of the reinforced foam, several parameters and procedures are important to produce implants with the desired integrity and mechanical properties. Preferably, the reinforcement material is substantially flat when placed in the mold. To ensure the proper degree of flatness, the reinforcement (e.g., mesh) is pressed flat using a heated press prior to its placement within the mold. Further, in the event that reinforcing structures are not isotropic it is desirable to indicate this anisotropy by marking the construct to indicate directionality. This can be accomplished by embedding one or more indicators, such as dyed markings or dyed threads, within the woven reinforcements. The direction or orientation of the indicator will indicate to a surgeon the dimension of the implant in which physical properties are superior.

As noted above, the manner in which the polymer solution is added to the mold prior to lyophilization helps contribute to the creation of a tissue implant with adequate mechanical integrity. Assuming that a mesh reinforcing material will be used, and that it will be positioned between two thin (e.g., 0.75 mm) shims it should be positioned in a substantially flat orientation at a desired depth in the mold. The polymer solution is poured in a way that allows air bubbles to escape from between the layers of the foam component. Preferably, the mold is tilted at a desired angle and pouring is effected at a controlled rate to best prevent bubble formation. One of ordinary skill in the art will appreciate that a number of variables will control the tilt angle and pour rate. Generally, the mold should be tilted at an angle of greater than about 1 degree to avoid bubble formation. In addition, the rate of pouring should be slow enough to enable any air bubbles to escape from the mold, rather than to be trapped in the mold.

If a mesh material is used as the reinforcing component, the density of the mesh openings is an important factor in the formation of a resulting tissue implant with the desired mechanical properties. A low density, or open knitted mesh material, is preferred. One preferred material is a 90:10 copolymer of glycolide and lactide, sold under the tradename VICRYL (Ethicon, Inc., Somerville, N.J.). One exemplary low density, open knitted mesh is Knitted VICRYL VKM-M, available from Ethicon, Inc., Somerville, N.J. Other preferred materials are polydioxanone or 95:5 copolymer of lactide and glycolide.

The density or "openness" of a mesh material can be evaluated using a digital photocamera interfaced with a computer. In one evaluation, the density of the mesh was determined using a Nikon SMZ-U Zoom with a Sony digital photocamera DKC-5000 interfaced with an IBM 300PL computer. Digital images of sections of each mesh magnified to 20× were manipulated using Image-Pro Plus 4.0 software in order to determine the mesh density. Once a digital image was captured by the software, the image was thresholded such that the area accounting for the empty spaces in the mesh could be subtracted from the total area of the image. The mesh density was taken to be the percentage of the remaining digital image. Implants with the most desirable mechanical properties were found to be those with a mesh density in the range of about 12 to 80% and more preferably about 45 to 80%.

In one embodiment, the preferred scaffold for cartilage repair is a mesh reinforced foam. More preferably, the foam is reinforced with a mesh that includes polydioxanone (PDO) and the foam composition is a copolymer of 35:65 ε-caprolactone and glycolide. For articular cartilage, the preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. Preferably, the mesh layer has a mesh density in the range of about 12 to 80% and more preferably about 45 to 80%.

In another embodiment, the preferred scaffold for cartilage repair is a nonwoven structure. More preferably, the composition of the nonwoven structure are PANACRYL, a 95:5 copolymer of lactide and glycolide, VICRYL, a 90:10 copolymer of glycolide and lactide, or a blend of polydioxanone and VICRYL sold under the tradename ETHISORB (Johnson & Johnson International, Belgium). For articular cartilage, the preferred structure to allow cell and tissue ingrowth is one that has an open pore structure and is sized to sufficiently allow cell migration. A suitable pore size for the nonwoven scaffold is one in which an average diameter is in the range of about 50 to 1000 microns and more preferably between about 100 to 500 microns. The nonwoven scaffold has a thickness between about 300 microns and 2 mm, and more preferably, between about 500 microns and 1.5 mm.

In one embodiment, the preferred scaffold for meniscus repair is a mesh reinforced foam. More preferably, the foam is reinforced foam with a mesh that includes polydioxanone (PDO) and the foam composition is a copolymer of 35:65 ε-caprolactone and glycolide. The preferred structure to allow cell and tissue ingrowth is one that has an open pore structure and is sized to sufficiently allow cell migration. A suitable pore size is one in which an average diameter is in the range of about 50 to 1000 microns, and more preferably, between about 50 to 500 microns. The mesh layer has a thickness in the range of about 1 micron to 1000 microns. Preferably, the foam has a thickness in the range of about 300 microns to 2 mm, and more preferably, between about 500 microns and 1.5 mm. In this embodiment, the preferred method of use is to surround the minced cartilage tissue with this scaffold material. Preferably, the mesh layer has a mesh density in the range of about 12 to 80% and more preferably about 45 to 80%.

One of ordinary skill in the art will appreciate that the selection of a suitable material for forming the biocompatible scaffold of the present invention depends on several factors. These factors include in vivo mechanical performance; cell response to the material in terms of cell attachment, proliferation, migration and differentiation; biocompatibility; and optionally, bioabsorption (or biodegradation) kinetics. Other relevant factors include the chemical composition, spatial distribution of the constituents, the molecular weight of the polymer, and the degree of crystallinity.

In addition to the biocompatible scaffold, the tissue repair implants of the present invention further include at least one sample of viable tissue that is associated with at least a portion of the scaffold. The term "viable," as used herein, refers to a tissue sample having one or more viable cells. Virtually any type of tissue can be used to construct the tissue repair implants of the present invention. Preferably, the tissue used is selected from cartilage tissue, meniscal tissue, ligament tissue, tendon tissue, skin tissue, bone tissue, muscle tissue, periosteal tissue, pericardial tissue, synovial tissue, nerve tissue, fat tissue, kidney tissue, bone marrow, liver tissue, bladder tissue, pancreas tissue, spleen tissue, intervertebral disc tissue, embryonic tissue, periodontal tissue, vascular tissue, blood and combinations thereof. In one embodiment useful for cartilage repair, the tissue is free of bone tissue and is selected from the group consisting of fibrocartilage tissue containing chondrocytes, meniscal tissue, ligament tissue and tendon tissue. The tissue used to construct the tissue implant can be autogeneic tissue, allogeneic tissue, or xenogeneic tissue. For example, healthy cartilage tissue, bone marrow tissue or aspirates are suitable for use with tissue repair implants for repairing condylar surfaces.

In one embodiment useful for meniscal repair, the tissue used in the tissue repair implant can be selected from the group consisting of meniscal tissue, cartilage tissue, skin, synovial tissue, periosteal tissue, pericardial tissue, fat tissue, bone marrow, blood, tendon tissue, ligament tissue, or combinations thereof. The tissue can be obtained using any of a variety of conventional techniques, such as for example, by biopsy or other surgical removal. Preferably, the tissue sample is obtained under aseptic conditions. Once a sample of living tissue has been obtained, the sample can then be processed under sterile conditions to create a suspension having at least one minced, or finely divided, tissue particle. The particle size of each tissue fragment can vary, for example, the tissue size can be in the range of about 0.1 and 3 $mm^3$, in the range of about 0.5 and 1 $mm^3$, in the range of about 1 to 2 $mm^3$, or in the range of about 2 to 3 $mm^3$, but preferably the tissue particle is less than 1 $mm^3$.

Preferably, the minced tissue has at least one viable cell that can migrate from the tissue fragment onto the scaffold. More preferably, the tissue contains an effective amount of cells that can migrate from the tissue fragment and begin populating the scaffold after implantation. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the scaffold material. Suitable matrix-digesting enzymes that can be used in the present invention include, but are not limited to, collagenase, metalloproteinase, chondroitinase, trypsin, elastase, hyaluronidase, petidase, thermolysin and protease.

In one embodiment, the minced tissue particles can be formed as a suspension in which the tissue particles are associated with a physiological buffering solution. Suitable physiological buffering solutions include, but are not limited to, saline, phosphate buffer solution, Hank's balanced salts, Tris buffered saline, Hepes buffered saline and combinations thereof. In addition, the tissue can be minced in any standard cell culture medium known to those having ordinary skill in the art, either in the presence or absence of serum. Prior to depositing the suspension of minced tissue on the scaffold or at the site of tissue injury, the minced tissue suspension can be filtered and concentrated, such that only a small quantity of physiological buffering solution remains in the suspension to prevent the tissue particles from drying out, and the minced tissue particles can be directly applied to the scaffold or site of injury. Preferably, the minced tissue particles are loaded at a concentration in the range of approximately 1 to 100 $mg/cm^2$, and more preferably in the range of about 1 to 20 $mg/cm^2$.

The suspension of minced living tissue can be used to create a tissue repair implant according to the present invention by depositing the suspension of living tissue upon a biocompatible scaffold, such that the tissue and the scaffold become associated. Preferably, the tissue is associated with at least a portion of the scaffold. The tissue repair implant can be implanted in a subject immediately, or alternatively, the construct can be incubated under sterile conditions for a duration and under conditions that are effective to maintain the viability of the tissue sample. In embodiments where the construct is incubated, the incubation conditions can vary, but preferably, the construct is incubated for a duration in the range of 1 hour to 6 weeks, and more preferably between about 1 week and 6 weeks, at a temperature in the range of about 20 to 40° C., and in an atmosphere containing between about 5 and 10% carbon dioxide ($CO_2$) and high humidity, e.g., approximately 100% humidity.

A kit can be used to assist in the preparation of the tissue repair implants of the present invention. According to the present invention, the kit includes a sterile container that houses one or more biocompatible scaffolds, a harvesting tool for collecting the living tissue sample from a subject, and one or more reagents for sustaining the viability of the tissue sample. Suitable reagents for sustaining the viability of the tissue sample include a physiological solution, such as for example, saline, phosphate buffering solution, Hank's balanced salts, standard cell culture medium, Dulbecco's modified Eagle's medium, ascorbic acid, HEPES, nonessential amino acid, L-proline, fetal bovine serum, autologous serum, and combinations thereof. The kit can also include a processing tool for dividing the tissue into minced tissue particles, or alternatively, the harvesting tool can be adapted to collect the tissue sample and to process the sample into finely divided tissue particles. The kit can, optionally, also include a delivery device for transferring the scaffold from the sterile container to a subject for implantation.

A biological component may, optionally, be incorporated within the tissue repair implants of the present invention. Preferably, the biological component is incorporated within, or coated on, the scaffolds disclosed above. In embodiments where the biological component is coated onto the scaffold, the biological component is preferably associated with at least a portion of the scaffold. By way of nonlimiting example, the biocompatible scaffold can include an adhesion agent for anchoring the suspension of minced tissue fragments to the scaffold. Preferably, the adhesion agent is an anchoring agent, a cross-linking agent (i.e., chemical or physical), and combinations thereof.

Suitable anchoring agents include, but are not limited to, hyaluronic acid, fibrin glue, fibrin clot, blood clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

Suitable cross-linking agents include, for example, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof.

The biological components used in the present invention can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of effectors present within the implant of the present invention can include heterologous or autologous growth factors, proteins (including matrix proteins), peptides, antibodies, enzymes, platelets, glycoproteins, hormones, cytokines, glycosaminoglycans, nucleic acids, analgesics, viruses, virus particles, and cell types. It is understood that one or more effectors of the same or different functionality may be incorporated within the implant.

Examples of suitable effectors include the multitude of heterologous or autologous growth factors known to promote healing and/or regeneration of injured or damaged tissue. These growth factors can be incorporated directly into the biocompatible scaffold, or alternatively, the biocompatible scaffold can include a source of growth factors, such as for example, platelets. Exemplary growth factors include, but are not limited to, TGF-β, bone morphogenic protein, cartilage-derived morphogenic protein, fibroblast growth factor, platelet-derived growth factor, vascular endothelial cell-derived growth factor (VEGF), epidermal growth factor, insulin-like growth factor, hepatocyte growth factor, and fragments thereof. Suitable effectors likewise include the agonists and antagonists of the agents noted above. The growth factor can also include combinations of the growth factors listed above. In addition, the growth factor can be autologous growth factor that is supplied by platelets in the blood. In this case, the growth factor from platelets will be an undefined cocktail of various growth factors. Platelets are normally found in the blood and play a role in hemostasis and wound healing. During clot formation, the platelets become activated and release growth factors such as PDGF, TGF-β, VEGF, and IGF. Platelets can be separated from blood using techniques such as centrifugation. When platelet rich plasma (PRP) is combined with an activator, a platelet clot is created. An activator can be, but is not limited to, thrombin, adenosine di-phosphate (ADP), collagen, epinephrine, arachidonic acid, Ristocetin, calcium, and combinations thereof.

The proteins that may be present within the implant include proteins that are secreted from a cell or other biological source, such as for example, a platelet, which is housed within the implant, as well as those that are present within the implant in an isolated form. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one of ordinary skill in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as effectors according to the present invention. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

The biocompatible scaffolds of the present invention can also have cells incorporated therein. Suitable cell types that can serve as effectors according to this invention include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells. Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The tissue implants of the invention can also be used in gene therapy techniques in which nucleic acids, viruses, or virus particles deliver a gene of interest, which encodes at least one gene product of interest, to specific cells or cell types. Accordingly, the biological effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold of the tissue repair implant, the implant can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One of ordinary skill in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One of ordinary skill in the art will appreciate that the identity of the biological component may be determined by a surgeon, based on principles of medical science and the applicable treatment objectives.

The biological component or effector of the issue repair implant can be incorporated within the scaffold before or after manufacture of the scaffold, or before or after the surgical placement of the implant.

Prior to surgical placement, the biocompatible scaffold can be placed in a suitable container comprising the biological component. After an appropriate time and under suitable conditions, the scaffold will become impregnated with the biological component. Alternatively, the biological component can be incorporated within the scaffold by, for example, using an appropriately gauged syringe to inject the biological agent(s) into the scaffold. Other methods well known to those of ordinary skill in the art can be applied in order to load a scaffold with an appropriate biological component, such as mixing, pressing, spreading, centrifuging and placing the biological component into the scaffold. Alternatively, the biological component can be mixed with a gel-like carrier prior to injection into the scaffold. The gel-like carrier can be a biological or synthetic hydrogel, including an alginate, a cross-linked alginate, hyaluronic acid, collagen gel, fibrin glue, fibrin clot, poly(N-isopropylacrylamide), poly(oxyalkylene), agarose, chitin, chitosan, cellulose, polysaccharides, poly(oxyalkylene), a copolymer of poly(ethylene oxide)-poly(propylene oxide), poly(vinyl alcohol), polyacrylate, platelet poor plasma (PPP) clot, laminin, solubilized basement membrane, and combinations thereof.

Following surgical placement, an implant wherein the biocompatible scaffold is devoid of any biological component can be infused with biological agent(s), or an implant wherein the scaffold includes at least one biological component can be augmented with a supplemental quantity of the biological component. One method of incorporating a biological component within a surgically installed implant is by injection using an appropriately gauged syringe.

The amount of the biological component included with a biocompatible scaffold will vary depending on a variety of factors, including the size of the scaffold, the material from which the scaffold is made, the porosity of the scaffold, the identity of the biologically component, and the intended purpose of the tissue repair implant. One of ordinary skill in the art can readily determine the appropriate quantity of biological component to include within a biocompatible scaffold for a given application in order to facilitate and/or expedite the healing of tissue. The amount of biological component will, of course, vary depending upon the identity of the biological component and the given application.

In another embodiment, the tissue repair implant can include an additional retaining element that is placed over the tissue-laden scaffold. Preferably, in this embodiment, at least a portion of the tissue suspension is associated with at least a portion of the outer surface of the scaffold, such that the tissue suspension is "sandwiched" between the biocompatible scaffold and the retaining element. The retaining element can be formed from virtually any biocompatible material, and in one embodiment, the retaining element can be formed using tissue grafts, including grafts obtained from allogeneic tissue, autogeneic tissue, and xenogeneic tissue, an additional biocompatible scaffold selected from the biocompatible scaffolds disclosed above, and combinations thereof. In another embodiment, the retaining element can be a porous mesh, a porous mesh-like material, such as for example, a knit, a weave, a nonwoven, or a thin, perforated elastomeric sheet having pores or perforations to allow tissue ingrowth. The thin, perforated elastomeric sheets are preferably constructed from collagen or silk or blends or copolymers of polylactic acid (PLA), polyglycolic acid (PGA), polycaprolactone (PCL) and polydioxanone (PDO). The type of retaining element used can vary according to the desired tissue repair. By way of non-limiting example, in one embodiment for meniscus repair, the retaining element can be a mesh-reinforced foam. In another embodiment, the retaining element can be a mesh structure. These retaining elements can be placed over the biocompatible scaffold, or alternatively, the retaining element can be affixed, such as for example, by suturing or stapling, the implant to act as a retaining element. One of ordinary skill in the art will appreciate that additional processing of the retaining element, such as for example, the placement of holes within the retaining element, may be determined by a surgeon, based on principles of medical science and the applicable treatment objectives.

In yet another embodiment, an electrostatically spun fabric barrier may be added to the implant to act as a barrier to hyperplasia and tissue adhesion, thus reducing the possibility of postsurgical adhesions. The fabric barrier is preferably in the form of dense fibrous fabric that is added to the implant. Preferably, the fibrous fabric is comprised of small diameter fibers that are fused to the top and/or bottom surface of the biocompatible scaffold. This enables certain surface properties of the structure, such as porosity, permeability, degradation rate and mechanical properties, to be controlled.

One of ordinary skill in the art will appreciate that the fibrous fabric can be produced via an electrostatic spinning process in which a fibrous layer can be built up on lyophilized foam and nonwoven surfaces. This electrostatic spinning process may be conducted using a variety of fiber materials. Exemplary fiber materials include aliphatic polyesters. A variety of solvents may be used as well, including those identified above that are useful to prepare the polymer solution that forms the foam component.

The composition, thickness, and porosity of the fibrous layer may be controlled to provide the desired mechanical and biological characteristics. For example, the bioabsorption rate of the fibrous layer may be selected to provide a longer or shorter bioabsorption profile as compared to the underlying biocompatible scaffold. Additionally, the fibrous layer may provide greater structural integrity to the composite so that mechanical force may be applied to the fibrous side of the structure. In one embodiment the fibrous layer could allow the use of sutures, staples or various fixation devices to hold the composite in place. Generally, the fibrous layer has a thickness in the range of about 1 micron to 1000 microns.

The tissue repair implant of the present invention can be used for resurfacing a diseased or damaged articular surface in a patient, and the tissue repair implant is configured to cover substantially an entire surface area of the prepared articular surface where diseased cartilage tissue has been removed.

In one embodiment of the present invention, the tissue repair implant is used in the treatment of a tissue injury, such as injury to a ligament, tendon, nerve, skin, cartilage or meniscus. Repairing tissue injuries involves the steps of obtaining a sample of living tissue by any of the variety of techniques known to those having ordinary skill in the art, processing that sample of living tissue under sterile conditions, such as for example by cutting the tissue, to create at least one minced, finely divided tissue particle, depositing the tissue sample upon the biocompatible scaffold, such that the tissue sample becomes associated with the scaffold to form a tissue repair implant, and placing the tissue repair implant in a desired position relative to the tissue injury. Repairing tissue injuries may also involve placing the scaffold at the site of tissue injury and then depositing the fine tissue particles onto the scaffold. The cells in the tissue particles associated with the scaffold can migrate to the scaffold and begin proliferating and integrating with surrounding tissue at the site of implantation, thereby repairing the tissue injury. This method for repairing tissue injuries can include an additional, optional step. Prior to the step of placing the tissue repair implant in a desired position relative to the tissue injury, the scaffold and associated tissue particles can be incubated for a duration and under conditions effective to allow cells within the tissue particles to migrate from the tissue and begin populating the scaffold. In an exemplary embodiment of the present invention, the tissue repair implant is used for resurfacing a diseased or damaged articular surface in a patient, and the tissue repair implant is configured to cover substantially an entire surface area of the articular surface. In the context of articular resurfacing, the method of the invention is particularly applicable to the resurfacing and/or repair of relatively large areas of defective cartilage, such as those having a surface area in the range of about 10 to 20 cm$^2$.

The tissue samples used in the present invention are obtained from a donor (autogenic, allogeneic, or xenogeneic) using appropriate harvesting tools. The tissue samples can be finely minced and divided into small particles either as the tissue is collected, or alternatively, the tissue sample can be minced after it is harvested and collected outside the body. In embodiments, where the tissue sample is minced after it is harvested, the tissue samples can be weighed and then washed three times in phosphate buffered saline. Approximately 300 to 500 mg of tissue can then be minced in the presence of a small quantity, such as, for example, about 1 ml, of a physiological buffering solution, such as, for example, phosphate buffered saline, or a matrix digesting enzyme, such as, for example, 0.2% collagenase in Hams F12. Mincing the tissue divides the tissue into particles or small pieces of approximately 1 mm$^3$. Mincing the tissue can be accomplished by a variety of methods. In one embodiment, the mincing is accomplished with two sterile scalpels using a parallel direction, and in another embodiment, the tissue can be minced by a processing tool that automatically divides the tissue into particles of a desired size. In one embodiment, the minced tissue can be separated from the physiological fluid and concentrated using any of a variety of methods known to those having ordinary skill in the art, such as for example, sieving, sedimenting or centrifuging. In embodiments where the minced tissue is filtered and concentrated, the suspension of minced tissue preferably retains a small quantity of fluid in the suspension to prevent the tissue from drying out. In another embodiment, the suspension of minced tissue is not concentrated, and the minced tissue can be directly delivered to the site of tissue repair via a high concentration tissue suspension or other carrier such as for example, a hydrogel, fibrin glue, or collagen. In this embodiment, the minced tissue suspension can be covered by any of the biocompatible scaffolds described above to retain the tissue fragments in place.

The minced tissue can then be distributed onto a scaffold using a cell spreader so as to cover the entire scaffold. In a preferable embodiment for meniscus and cartilage repair, the minced tissue is spread onto 4×5 cm scaffolds that have been presoaked in Dulbecco's modified Eagles medium (DMEM) so as to cover the entire scaffold. Optionally, the tissue particles can be adhered to the scaffolds using any of the adhesive agents described above, such as, for example, fibrin glue or platelet rich plasma. In embodiments using fibrin glue or platelet rich plasma, a few microliters of thrombin can be placed on the scaffolds, prior to distribution of fibrinogen or platelet rich plasma on the scaffolds, and allowed to set. Once the tissue particles and any additional agents have been deposited on the scaffold, the tissue repair implant can then implanted immediately, or alternatively, the implant can be cultured in vitro for a duration and under conditions sufficient to allow the cells in the tissue particles to migrate from the tissue particles onto the scaffold. In an embodiment where the tissue repair implant is incubated prior to implantation, the implant is preferably cultured in vitro for approximately 1-3 weeks in a chondrocyte growth medium, such as for example, DMEM-high glucose, supplemented with 20% fetal calf serum (FCS), 10 mM HEPES, 0.1 mM nonessential amino acids, 20 mg/ml of L-proline, 50 mg/ml ascorbic acid, 100 mg/ml penicillin, 100 mg/ml of streptomycin and 0.25 mg/ml of amphotericin B.

The methods of repairing tissue injuries using the tissue implants according to the present invention can be conducted during a surgical operation to repair the tissue injury. Alternatively, the steps of processing the tissue sample to create minced, finely divided tissue particles, depositing the tissue particles upon the scaffold to form a tissue repair implant, and/or incubating the tissue repair implant prior to implantation can be conducted at another, sterile location prior to surgical placement of the implant relative to the site of injury.

The implants used to repair injured tissue can be of a size and shape such that they match the geometry and dimensions of a desired portion or lesion of the tissue to be treated. The implant can be sized and shaped to produce the necessary geometry by numerous techniques including cutting, folding, rolling, or otherwise manipulating the implant. As noted above, the biological component may be added to the scaffold during or after manufacture of the scaffold or before or after the implant is installed in a patient. An additional quantity of the biological component may be added after the implant is installed. Once access is made into the affected anatomical site (whether by minimally invasive, open or mini-open surgical technique), the implant can be affixed to a desired position relative to the tissue injury, such as within a tear or lesion. Once the implant is placed in the desired position or lesion, it can be affixed by using a suitable technique that allows implant retention in a mechanically dynamic environment. In one aspect, the implant can be affixed by a chemical and/or mechanical fastening technique. Suitable chemical fasteners include glues and/or adhesive such as fibrin glue, fibrin clot, and other known biologically compatible adhesives. Suitable mechanical fasteners include sutures, staples, tissue tacks, suture anchors, darts, screws, pins and arrows. It is understood that combinations of one or more chemical and/or mechanical fasteners can be used. Alternatively, one need not use any chemical and/or mechanical fasteners. Instead, placement of the implant can be accomplished through an interference fit of the implant with an appropriate site in the tissue to be treated.

In one use, the tissue repair implant can be used for repairing and replacing damaged or diseased cartilage tissue at an articular surface during articular resurfacing surgery or it can be used as a stand alone device. In the case of repair, damaged or diseased cartilage tissue on the articular surface of a bone joint is removed during surgery, along with fibrillation and fissuring wounds. The articular surface is debrided and prepared to expose a subchondral bone surface that will receive the tissue repair implant. Prior to placement of the implant, the subchondral bone surface can be treated with marrow stimulation techniques such as by forming microfractures or drilling to provide an abrasion on the surface. The marrow stimulation techniques enable cellular contribution from the marrow cells to the tissue repair process. The implant provides mechanical support to the joint while also enabling new cartilage to grow within the implant and eventually replace the implant with new tissue having similar mechanical properties to that of native cartilage tissue. The implant provides the mechanical support that is initially necessary to ensure proper joint function, and also serves as a guide for tissue regeneration. In another use as a stand alone device, the diseased cartilage tissue is removed from the articular surface, and the tissue repair implant with minced cartilage tissue serves to replace the function of the damaged cartilage. The minced cartilage tissue serves as the tissue source for the growth of new cartilage tissue.

The implants of the present invention can also be used as a delivery device for a therapeutic, wherein the therapeutic is the minced tissue, which includes a combination of cells, extracellular matrix and inherent growth factors. The scaffold portion of the implant can allow for hormones and proteins to be released into the surrounding environment.

The methods of repairing tissue injuries using the tissue implants according to the present invention can be conducted during a surgical operation to repair the tissue injury. FIG. 1 illustrates an exemplary method of resurfacing a diseased or damaged articular surface in a patient who has been diagnosed with an isolated cartilage lesion (and does not have an anterior cruciate ligament (ACL) rupture or torn meniscus damage). As shown, the patient is prepared for tissue repair surgery in a conventional manner using conventional surgical techniques. Tissue repair is performed at the site of injured tissue using the tissue repair implants of the present invention. In the present example shown, the site of tissue injury is the condylar surface 10 of the patient's knee joint. Using appropriate tools such as the harvesting tool 20 shown, a tissue sample can be harvested from the patient (or another donor) to form the tissue repair implant 30. Preferably, the tissue comprises healthy cartilage tissue. The tissue sample is finely minced and divided into at least one tissue particle having a particle size in the range of about 0.1 to 3 $mm^3$. The tissue can be minced using a conventional mincing technique such as two sterile scalpels used in a parallel direction. Between about 300 to 500 mg of tissue is minced in the presence of about 1 ml of a physiological buffering solution, depending on the extent of the tissue injury at the site of repair. The minced tissue is filtered and concentrated to separate the minced tissue particle from the physiological buffering solution. The minced tissue can be concentrated using any of a variety of conventional techniques, such as for example, sieving, sedimenting or centrifuging. The minced tissue particles are then distributed using a cell spreader or tissue disperser 40 as shown in FIG. 1. A 4×5 cm biocompatible scaffold 32 can be held within the disperser 40, such as within a holding ring 22, and soaked in Dulbecco's modified Eagles medium (DMEM). An adhesion agent 50 such as platelet rich plasma (PRP) can be added to the biocompatible scaffold and the minced tissue particles.

To prepare the articular surface 12 for receiving the tissue repair implant, the articular surface 12 can be debrided to expose a subchondral bone surface 14. If desired, one or more holes can be formed on the exposed subchondral bone surface 14 to induce bleeding and effect marrow cell infiltration. The tissue repair implant 30 is then implanted at the site of tissue injury, either immediately or after a period of in vitro incubation. Preferably, the size of the tissue repair implant 32 placed within the prepared area will generally conform to the size and shape of the defect and/or the prepared area. As shown in FIG. 1, the side of the implant 32 with the layer of minced tissue should be placed down on the prepared subchondral bone surface 14. If desired, the implant can then be secured in place using one or more fastening agents. Suitable fastening agents include fasteners, staples, tissue tacks, suture, adhesive, and combinations thereof. For example, a biocompatible, bioabsorbable staple 60 as illustrated in FIG. 1 can be applied to secure the tissue loaded implant 30 onto the prepared subchondral surface 14. The secured implant can be trimmed around its edges using a scalpel. Additionally, a sealing agent such as fibrin glue can be applied to seal the implant around the edges. Final wound closure is performed in a conventional manner using conventional surgical techniques.

The following examples are illustrative of the principles and practice of this invention. Numerous additional embodiments within the scope and spirit of the invention will become apparent to those skilled in the art.

Example 1

The primary objective of this study was to test implant retention for resurfacing large chondral defects in a high weight-bearing condyle area such as in the knee joint.

A. Creation of Chondral Defect

Defects were created on weight bearing contour of the medial femoral condyle (MFC) of eight (8) goats. The MFC's were accessible from medial arthrotomy in a randomly assigned stifle. The removal of full thickness cartilage (ICRS Grade 3) was achieved by the use of scalpel and curettage. Cartilage was manually removed to the level of subchondral tidemark, but to make sure that the bone was not visibly exposed. Two sizes of defect were tested in this study, 20×20 mm rectangular and 7 mm circular. There was one defect per stifle per goat.

B. Implant Preparation

For this implant retention test implants were prepared by loading fibrin glue onto the pre-wetted scaffold of appropriate sizes. The composition of the scaffolds used was a 95:5 copolymer of lactide and glycolide formed in a non-woven structure, which provides a favorable structural environment for cell ingrowth, infiltration or migration into and out of the scaffolds. No cells, tissue fragments or bioactives were loaded with these implants for the purpose of this study. Fibrin glue was applied to facilitate the adhesion of the implant to the subchondral bone surface.

C. Implant Resurfacing and Affixation

The implants, which were slightly larger in size than the defects, were placed on the defects and secured to the subchondral bone with staples. For the larger defect (20×20 mm), 5 to 6 staples were used and only 1 staple was used for the smaller (7 mm) defect. Finally the extra scaffold material on the peripheral edges was trimmed with surgical scissors to ensure a smooth connection and transition between the implant surface and adjacent native cartilage.

D. Post-Operative Rehabilitation

A fiberglass cast/Schroeder-Thomas Splint was applied post-operatively to each of the treated animals for two to four-weeks depending on the rehab protocols. The fiberglass cast/Schroeder-Thomas Splint was examined daily on individual goats to make sure the operated limb was free from direct weight loading. The rehabilitation protocol used for these goats called for two weeks of immobilization after the surgeries. These goats were walking for another two weeks without any immobilizing measure before euthanasia.

E. Summary of the Results

Both gross and histology analyses showed that implant retention with 7 mm circular defect was perfect even in the MFC area. Signs of intact staples and scaffold fibers were observed in all the cases.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for resurfacing a diseased or damaged articular surface in a patient, comprising the steps of: providing a biocompatible, bioresorbable scaffold, the scaffold comprising a flexible sheet; collecting and mincing living tissue comprising viable cells to form a plurality of minced tissue fragments having an effective amount of said viable cells such that said viable cells can migrate out of the minced tissue fragments and populate the scaffold, the plurality of minced tissue fragments comprising particles in the range from at least about 0.1 mm$^3$ to at least about 3 mm$^3$; immediately following the mincing step, associating the scaffold with at least one of the plurality of minced tissue fragments, wherein the at least one of the plurality of minced tissue fragments is distributed on a surface of the scaffold, thus forming a tissue repair implant; following the associating, placing at least one layer of a retaining element over at least a portion of the scaffold; preparing the articular surface to receive the tissue repair implant, wherein the surface area of the prepared articular surface is in the range of about 10 cm$^2$ to about 20 cm$^2$; after the placing and immediately after preparing the articular surface, implanting the tissue repair implant onto the prepared articular surface, wherein the scaffold is configured to (i) substantially conform to the prepared articular surface and (ii) substantially cover an entire surface area of the prepared articular surface; and securing the tissue repair implant in place using at least one mechanical biocompatible, fastening agent; wherein the tissue repair implant includes at least one biological component in association with the scaffold; wherein the biocompatible scaffold further comprises at least one additional biological component applied thereto; and wherein the at least one additional biological component comprises platelets, and further wherein the platelets are delivered in a biological or synthetic hydrogel selected from the group consisting of alginate, cross-linked alginate, hyaluronic acid, collagen gel, fibrin glue, fibrin clot, poly(N-isopropylacrylamide), agarose, chitin, chitosan, cellulose, polysaccharides, poly(oxyalkylene), a copolymer of poly(ethylene oxide)-poly(propylene oxide), poly(vinyl alcohol), polyacrylate, platelet poor plasma (PPP) clot, laminin, solubilized basement membrane, and combinations thereof.

2. The method of claim 1, wherein the biological component further includes an activator of platelets.

3. The method of claim 2, wherein the activator of platelets is selected from the group consisting of thrombin, adenosine di-phosphate (ADP), collagen, epinephrine, arachidonic acid, ristocetin, and combinations thereof.

4. A method for resurfacing a diseased or damaged articular surface in a patient, comprising the steps of: providing a biocompatible, bioresorbable scaffold, the scaffold comprising a flexible sheet; collecting and mincing living tissue comprising viable cells to form a plurality of minced tissue fragments having an effective amount of said viable cells such that said viable cells can migrate out of the minced tissue fragments and populate the scaffold, the plurality of minced tissue fragments comprising particles in the range from at least about 0.1 mm$^3$ to at least about 3 mm$^3$; immediately following the mincing step, associating the scaffold with at least one of the plurality of minced tissue fragments, wherein the at least one of the plurality of minced tissue fragments is distributed on a surface of the scaffold, thus forming a tissue repair implant; following the associating, placing at least one layer of a retaining element over at least a portion of the scaffold; preparing the articular surface to receive the tissue repair implant, wherein the surface area of the prepared articular surface is in the range of about 10 cm$^2$ to about 20 cm$^2$; after the placing and immediately after preparing the articular surface, implanting the tissue repair implant onto the prepared articular surface, wherein the scaffold is configured to (i) substantially conform to the prepared articular surface and (ii) substantially cover an entire surface area of the prepared articular surface; and securing the tissue repair implant in place using at least one mechanical biocompatible, fastening agent; wherein the tissue repair implant includes at least one biological component in association with the scaffold; and wherein the biocompatible scaffold further comprises an adhesion agent for anchoring a suspension of tissue fragment to the biocompatible scaffold.

5. The method of claim 4, wherein the adhesion agent comprises an anchoring agent selected from the group consisting of hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, synthetic acrylate-based adhesives, platelet rich plasma (PRP), Matrigel, Monostearoyl Glycerol co-Succinate (MGSA), Monostearoyl Glycerol co-Succinate/polyethylene glycol (MGSA/PEG) copolymers, laminin, elastin, proteoglycans and combinations thereof.

6. The method of claim 4, wherein the adhesion agent comprises a chemical cross-linking agent selected from the group consisting of divinyl sulfone (DVS), polyethylene glycon divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, and combinations thereof.

7. A method for resurfacing a diseased or damaged articular surface in a patient, comprising the steps of: providing a biocompatible, bioresorbable scaffold, the scaffold comprising a flexible sheet; collecting and mincing living tissue comprising viable cells to form a plurality of minced tissue fragments having an effective amount of said viable cells such that said viable cells can migrate out of the minced tissue fragments and populate the scaffold, the plurality of minced tissue fragments comprising particles in the range from at least about 0.1 mm$^3$ to at least about 3 mm³; immediately following the mincing step, associating the scaffold with at least one of the plurality of minced tissue fragments, wherein the at least one of the plurality of minced tissue fragments is distributed on a surface of the scaffold, thus forming a tissue repair implant; following the associating, placing at least one layer of a retaining element over at least a portion of the scaffold; preparing the articular surface to receive the tissue repair implant, wherein the surface area of the prepared articular surface is in the range of about 10 cm² to about 20 cm²; alter the placing and immediately after preparing the articular surface, implanting the tissue repair implant onto the prepared articular surface, wherein the scaffold is configured to (i) substantially conform to the prepared articular surface and (ii) substantially cover an entire surface area of the prepared articular surface; and securing the tissue repair implant in place using at least one mechanical biocompatible, fastening agent.

* * * * *